US005827834A

United States Patent [19]
Falk et al.

[11] Patent Number: 5,827,834
[45] Date of Patent: Oct. 27, 1998

[54] METHOD OF USING HYALURONIC ACID OR ITS PHARMACEUTICALLY ACCEPTABLE SALTS FOR THE TREATMENT OF DISEASE

[75] Inventors: Rudolf Edgar Falk; Samuel S. Asculai, both of Toronto, Canada

[73] Assignee: Hyal Pharmaceutical Corporation, Mississauga, Canada

[21] Appl. No.: 286,263

[22] Filed: Aug. 5, 1994

Related U.S. Application Data

[63] Continuation of Ser. No. 675,908, Jul. 3, 1991.

[30] Foreign Application Priority Data

Sep. 21, 1989 [CA] Canada ...................................... 612307

[51] Int. Cl.$^6$ .................................................. A61K 31/715
[52] U.S. Cl. .................................... 514/54; 514/1; 424/80
[58] Field of Search ............................ 514/1, 54; 424/80

[56] References Cited

U.S. PATENT DOCUMENTS

| | | |
|---|---|---|
| 2,583,096 | 1/1952 | Hididian et al. . |
| 3,436,454 | 4/1969 | Nouvel . |
| 3,887,703 | 6/1975 | Manoussos et al. . |
| 4,141,973 | 2/1979 | Balazs . |
| 4,272,522 | 6/1981 | Balazs . |
| 4,303,676 | 12/1981 | Balazs . |
| 4,582,865 | 4/1986 | Balazs et al. . |
| 4,636,524 | 1/1987 | Balazs et al. . |
| 4,684,627 | 8/1987 | LeVeen et al. . |
| 4,711,780 | 12/1987 | Fahim . |
| 4,716,224 | 12/1987 | Sakurai et al. . |
| 4,725,585 | 2/1988 | Wenge et al. . |
| 4,736,024 | 4/1988 | Della Valle et al. . |
| 4,755,544 | 7/1988 | Makino et al. . |
| 4,795,741 | 1/1989 | Leschiner et al. . |
| 4,801,619 | 1/1989 | Lindblad . |
| 4,808,576 | 2/1989 | Schultz et al. . |
| 4,814,176 | 3/1989 | Makino et al. . |
| 4,840,941 | 6/1989 | Ueno et al. . |
| 4,851,521 | 7/1989 | della Valle et al. . |
| 4,853,226 | 8/1989 | Machida et al. . |
| 4,937,254 | 6/1990 | Sheffield et al. . |
| 4,946,870 | 8/1990 | Partain, III et al. . |
| 4,957,744 | 9/1990 | della Valle et al. . |
| 4,965,353 | 10/1990 | della Valle et al. . |
| 4,970,298 | 11/1990 | Silver et al. . |
| 5,095,037 | 3/1992 | Iwamitsu et al. . |
| 5,166,331 | 11/1992 | della Valle et al. . |
| 5,234,914 | 8/1993 | Gallina ...................................... 514/54 |

FOREIGN PATENT DOCUMENTS

| | | |
|---|---|---|
| 30806/84 | 7/1984 | Australia . |
| B-72117/87 | 12/1987 | Australia . |
| B-17459/88 | 12/1988 | Australia . |
| B17459/88 | 12/1988 | Australia . |
| B14534/88 | 11/1990 | Australia . |
| 1205031 | 5/1986 | Canada . |
| 1240929 | 8/1988 | Canada . |
| 2031880 | 12/1990 | Canada . |
| 0 138 572 | 4/1985 | European Pat. Off. . |
| 0 179 442 | 4/1986 | European Pat. Off. . |
| 0 197 718 | 10/1986 | European Pat. Off. . |
| 0 208 623 | 1/1987 | European Pat. Off. . |
| 0 216 453 | 4/1987 | European Pat. Off. . |
| 0 244 718 | 4/1987 | European Pat. Off. . |
| 0 224 987 | 6/1987 | European Pat. Off. . |
| 0 240 098 | 10/1987 | European Pat. Off. . |
| 0 265 116 | 4/1988 | European Pat. Off. . |
| 0 270 317 | 6/1988 | European Pat. Off. . |
| 0 285 357 | 10/1988 | European Pat. Off. . |
| 0 287 210 | 10/1988 | European Pat. Off. . |
| 0 295 092 | 12/1988 | European Pat. Off. . |
| 0 296 740 | 12/1988 | European Pat. Off. . |
| 0 312 208 | 3/1989 | European Pat. Off. . |
| 0 341 745 | 5/1989 | European Pat. Off. . |
| 0 378 852 | 7/1990 | European Pat. Off. . |
| 57-183707 | 11/1982 | Japan . |
| 61-000017 | 1/1986 | Japan . |
| 62-201825 | 9/1987 | Japan . |
| 1287041 | 1/1988 | Japan . |
| 63/045233 | 2/1988 | Japan . |
| A11678/88 | 5/1988 | Japan . |
| 116678/88 | 11/1989 | Japan . |
| 62-287041 | 11/1989 | Japan . |
| 769287 | 3/1957 | United Kingdom . |
| 1283892 | 8/1972 | United Kingdom . |
| 2099826 | 12/1982 | United Kingdom . |
| WO88/07060 | 9/1988 | WIPO . |
| WO89/05645 | 6/1989 | WIPO . |
| WO 89/07932 | 9/1989 | WIPO . |
| WO 91/04058 | 4/1991 | WIPO . |
| 9222585 | 12/1992 | WIPO .............................. C07N 1/00 |

OTHER PUBLICATIONS

Goodwin, J.S., Prostaglandin E and Cancer Growth: Potential for Immunotherapy with Prostaglandin Synthesis Inhibitors, *Augmentive Agents in Cancer Therapy*, Raven Press, New York (1981), pp. 393–415.

Asculai, Dr. S., "Inactivation of Herpes Simplex Viruses by Nonionic Surfactants", *Antimicobial Agents and Chemotherapy*, Apr. 1978, pp. 686–690.

Sneader, W.E., Chemical Abstracts, vol. 76, No. 10, Possible Mechanism for Action of DMSO on Percutaeous absorption, *J. Pharm. Pharmcol*, 1971, 23 (Supp).

U.S. application No. 07/338,106, Falk, Filed Apr. 1989.

International Preliminary Examination Report for PCT/CA90/00306 and attachement substitute claims.

Alaverdyan et al., "Effect of hyaluronidase, hyaluronic acid, and some other substancs on postradiational experimental bacteriemia", *Bulletin of Experimental Biology & Medicine* 1967: 64(9): 967–969.

(List continued on next page.)

*Primary Examiner*—Kathleen K. Fonda
*Attorney, Agent, or Firm*—Ivor M. Hughes; Marcelo K. Sarkis; Neil H. Hughes

[57] ABSTRACT

A method of treating anorectal disease is provided which comprises applying to anorectal tissue in need of such treatment an effective amount of a composition comprising a pharmaceutically acceptable carrier and hyaluronic acid or a pharmaceutically acceptable salt thereof in an amount8 of up to about 10% by weight.

6 Claims, 1 Drawing Sheet

OTHER PUBLICATIONS

Balazs et al, "The rheological properties and biological funtion of hyaluronic acid", *Chem. and Mol. Biol. of the Intercellular Matrix*, vol. 3, 1970, pp. 1241–1253.

Sandra Blakeslee, "Solid cores of tumors keeping out best drugs", Jul. 8, 1989 edition of the Globe and Mail, Toronto, Ontario, p. D4.

Pam Harrison, "Toxic drug tamed but still potent" *Ontario Medicine*, vol. 8, No. 16 dated Aug. 21, 1989, p. 1.

*The Merck Index* Eleventh Edition, Centennial Edition, Hyaluronic Acid formulation, pp. 751 and 752, 1989.

Alan R. Liss, Inc., Modulation of Immunity in Cancer Patients by Prostaglandin Antagonists, *Immunity to Cancer II*, Braun, D.P. et al., 1989, pp. 439–448.

Balezs E.A. et al, "Hyaluronic acid: Its structure and use", *Cosmetics & Toiletries*, Polymers in Cosmetics 1984; 99: 65–72.

Camber O. et al, "Diffusion of some low molecular weight compounds in sodium hyaluronate", *Acta Pharmaceutica Suecica* 1985; 22(6): 315–320.

Camber O. et al, "Influence of sodium hyaluronate on the meiotic effect of pilocarpine in rabbits", *Current Eye Research* 1987: 6(6): 779–784.

Chang S–C, "Prodrug and vehicle approaches to improve the therapeutic index of topically applied timolol in the pigmented rabbit", *Dissertation Abstracts International* 1988; 49(2): 367–B.

Cravioto R O et al, Effects of Precipitates Formed by Insulin with Hyaluronic Acid and Mucoid from Vitreous Humor in Depressing Blood–Sugar Levels *Science* (1950); vol. 111: 520–521.

Gieldanowski J et al, "Studies on immunosuppresive and anti–inflammatory effects of adriamycin", *Arch. Immunol. Ther. Exp.* (1980); 28(3): 439–446.

Hassan, H.G., et al., "Effects of adjuvants to local anaesthetics on their duration", *Acta Anaesthesiol Scand* 1985; 29: 384–388.

Hurd, E.R., "Immunosuppressive and antiinflammatory properties of cyclophosphamide, azathioprine and methotrexate", *Arthritis and Rheumatism* (1973 Jan./Feb. ); 16(1): 84–88.

Idson B, "Polymers in skin cosmetics", *Cosmetics & Toiletries* 1988; 103: 63–68.

Johansson A. et al, "Effects of adjuvants to local anaesthetics on their duration", *Acta Anaesthesiol Scand* 1985; 29: 736–738.

Kalbhen D.A., "The inhibitory effects of steroidal and non–steroidal antirheumatic drugs on articular cartilage in osteoarthrosis and its counteraction by a biological GAG–peptide complex (Rumalon®)", *Z. Rheumatol* (1982): 41: 202–211.

Katsu M. et al., "Significance and clinical use of non–steroid anti–inflammatory drugs as substitutes for steroids in steroid dependence", *Nippon Rinsho* (1986 Jan.) 26(1): 89–95.

Kreis H et al, "Nonsteroid antiinflammatory agents as a substitute treatment for steroids in ATGAM–treated cadaver kidney recipients" *Transplantation* (1984 Feb.); 37(2): 139–145.

McIlwraith W, "Current concepts in equine degenerative joint disease", *Journal of the Am. Veterinary Medical Assoc.* 1982; Feb. 1, vol. 180: 239–250.

Mizushima Y., "Possibility of non–steroid anti–inflammatory drugs as a substitute for steroids–analysis of the present situation and demands for the future", *Nippon Rinsho* (Jan. 1986); 26(1): 61–65.

Nizolek D.J.H. et al, "Corticosteroid and hyaluronic acid treatments in equine degenerative joint disease: A Review" *The Cornell Veterinarian* 1981: 71(4): 355–375.

Pigman W et al, "Acide hyaluronique et facteurs de permeabilite tissulaire" *Bull. Soc. Chim. Biol.* 1963; 45(2–3): 185–202.

Pruett RC, et al, "Hyaluronic acid vitreious substitute", In: *Vitreous Surgery and Advances in Fundus Diagnosis and Treatment*, H. McKenzie Freeman et al Editors, Appleton–Century–Crofts, 1977: Chapter 55, pp. 433–444.

Reim M et al, "Surgical procedures in the treatment of most severe eye burns" *Acta Ophthalmologica* 1989–Supplementum 192; 67: 47–54.

Rydell N et al, "Effect of intra–articular injection of hyaluronic acid on the clinical symptons of osteoarthritis and on grandulation tissue formation" *Clinical Orthopaedics and Related Research* 1971; 80 (Oct.): 25–29.

Saba P et al, "Investigation of antihyperlipemic activity of an association of clofibrate and extractive mucopolysaccharide complex", *Current Therapeutic Research* 1978; 23(4): 455–463.

Stegmann R et al, "Use of Sodium hyaluronate in sever penetrating ocular trauma" *Acta Ophthalmol.* 1986; 18: 9–13.

Trabucchi E et al, "Prevention of wound dehiscense in severely obese patients with jejuno–ileal by–pass: the role of hyaluronic acid" *Pharmatherapeutica* 1988; 5(4): 233–239.

Sertoli P et al., L'acido jaluronico, per uso topico, nella cura della ulcere trofocircolatorie degli arti inferiori (Comunicazioni) *Giornale Italiano di Dermatologia* 1970; 45(8): 468–471.

Walther M, "The Prevention of Strine Cutis Distansae During Pregnancy", *Minerva Ginecologica* (1981) vo. 33: 497–499.

Weirich E G et al, "Dermatopharmacology of salicyclic acid. III. Topical contra–inflammatory effects of salicylic acid and othe drugs in animal experiments", *Dermatologica* (1976); 152(2): 87–99.

International Preliminary Examination Report for PCT/CA90/00306 and attachment of substitute claims, no publication date.

*Physician's Desk Reference*, 49th Edition, Medical Economics Data Production Company, pp. 1566–1570, 1995.

Goodwin et al (eds.) "The Pharmacological Basis of Therapeutics", MacMillan Publishing Co., Inc., New York, 1975, pp. 325–332 & 1365.

Weigel et al., in "The Biology of Hyaluronan" (Evered et al., eds), CIBA Foundation Symposium 143 held 27–28 Sep., 1988, Published 1989, John Wiley & Sons Ltd. New York, pp. 248–264.

West et al (1989) Exp. Cell Res. 183 :179–196.

Verbeeck, R.K. Rectal Administration of NSAIDs (suppositories), 1992, Inflamm. Dis. Ther. Vo 10, pp. 447–460.

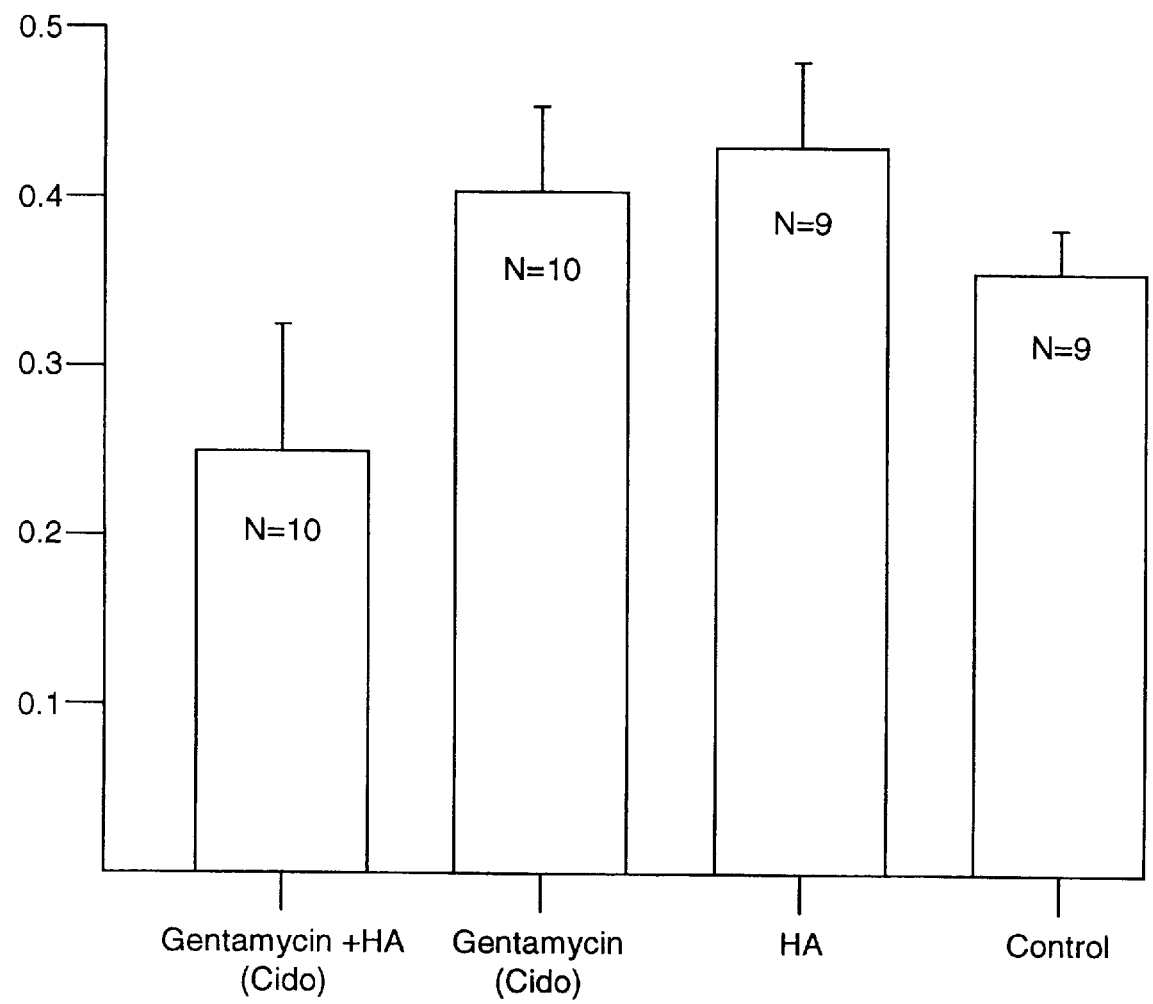

METHOD OF USING HYALURONIC ACID OR ITS PHARMACEUTICALLY ACCEPTABLE SALTS FOR THE TREATMENT OF DISEASE

This application is a continuation of application Ser. No. 07/675,908, filed Jul. 3, 1991, which is co-pending and is a national stage application based on International Application No. PCT/CA 90/00306 having an international filing date of Sep. 18, 1990.

FIELD OF INVENTION

The invention relates to, formulations suitable for use to treat conditions and disease, (for example cancer), the use of such formulations to treat conditions and disease, methods of treating conditions and disease, and the delivery of medicinal and therapeutic agents for the treatment of disease and conditions.

BACKGROUND OF THE INVENTION

In an article entitled "Solid cores of tumors keeping out best drugs" by Sandra Blakeslee published in the Jul. 8, 1989 edition of the Globe and Mail, Toronto, Ontario,. Ms. Blakeslee submitted that a growing number of researchers believe that a basic misunderstanding of the structure of solid tumors has led researchers into designing cancer drugs that are doomed to fail in many patients.

She relates that, Dr. Herberman, Director of the Pittsburgh Cancer Center, said that for decades, cancer researchers have simply developed drugs, put them in the bloodstream and assumed they would be carried to the tumor giving almost no consideration to how uniformly the drug is distributed once it reaches the tumor.

Her article also provided that according to Dr. Judah Folkman, a leading researcher on blood growth factors at the Harvard Medical School, for a long time, physicians have been taught that tumors outgrow their blood supply. According to the article that statement is not true. Tumors compress their blood supply. This compression makes it harder to administer drugs.

The article provides further that most people think a tumor is nothing but a collection of cancer cells. According to Dr. Jain, another researcher, in reality the tumor is only 50 per cent cells. The other half is blood vessels and interstitial space. Interstitial space in a tumor, he said, can be likened to the space between marbles packed in a box.

The article further provides that no matter how biological agents are mixed and administered, they must cross a blood-vessel wall and then cross the interstitium to reach their targets, cancer cells. The article continues that every tumor is different and there are different regions within each. Moreover, tumors change daily as they grow and rearrange parts. Most blood vessels inside tumors are highly disorganized as they take tortuous turns and grow peculiar attachments to nearby vessels.

In general, Dr. Jain said, as a tumor grows, its outer region recruits new blood vessels from surrounding normal tissue. It also forms several abnormal blood vessels of its own. As the tumor grows in a confined space, many of the twisted blood vessels near its center are crushed. In turn, the tumor cells near them appear to die, although they grow into active cancer if transplanted in other animals. High pressures build up in these necrotic regions. Both blood vessels and liquid plasma in the interstitial spaces are squeezed. The pressure, therefore, prevents blood-borne molecules, including oxygen, from entering the central tumor areas.

Pressure is not uniform in normal tissue, Dr. Jain said, so a large molecule such as an antibody would reach its target through convection induced by pressure differences. But in the center of a tumor, pressure is uniformly high, blocking convection.

Molecules also migrate by diffusion Dr. Jain said, which is similar to the way a drop of ink spreads in water.

But he indicated that he measured antibody diffusion in tumors and found that it can take days, weeks or months for such large molecules to reach uniform concentration by diffusion in tumors. By then, it may be too late for treatments to do any good.

Finally, the fluid that builds up in the interstitium slowly leaks out of the tumor, he said, washing away molecules trying to reach its center.

In our Canadian Patent Application Serial Number 568,512 we disclose a new formulation suitable for use for treating cancer (for use in conjunction with at least thermotherapy (hyperthermia) and if desired, other modalities (such as chemotherapy or radiation)), the formulation comprising (for example in a pharmaceutically acceptable carrier):

(a) a glucose inhibiting (non-toxic) amount of an agent that blocks the glucose transport protein (active transport molecule in the membrane) of a cell from transporting glucose into the cell, and (b) an effective (non-toxic) amount of an agent which (i) enhances penetration and transport of agent (a) through the tissue surrounding the various cellular elements, generally known as scar tissue or fibrous reaction around the cancerous tumor, and (ii) alters the penetration characteristics of the tissue surrounding the tumor to permit agent (a) to be transported to the center of the tumor.

We also disclosed a combination and formulation suitable for use for treating cancer, the combination comprising:

(a) a glucose inhibiting (non-toxic) amount to an agent that blocks the glucose transport protein (active transport molecule in the membrane) of a cell from transporting glucose into the cell, and (b) an effective (non-toxic) amount of an agent which (i) enhances penetration and transport of agent (a) through the tissue surrounding the various cellular elements, generally known as scar tissue or fibrous reaction around the cancerous tumor, and (ii) alters the penetration characteristics of the tissue surrounding the tumor to permit agent (a) to be transported to the center of the tumor.

After the introduction of the formulation or combination comprising agents (a) and (b) to the patient which have the effect of metabolically compromising the cancer cells of the tumor, the tumor and the cancer cells making up the tumor are stressed by at least thermotherapy (hyperthermia). In this regard, when agent (a) is transported into the tumor cells and the tumor cells are stressed, there is an inadequate amount of glucose available to the tumor cells for them to continue to function metabolically. Thus the tumor cell is impaired in its energy supply and dies. We also disclosed in the application a method for the treatment of cancer which method comprises administering (for example in a pharmaceutically acceptable carrier):

(a) a glucose inhibiting (non-toxic) amount of an agent that blocks the glucose transport protein (active transport molecule in the membrane) of a cell from transporting glucose into the cell, and (b) an effective (non-toxic) amount of an agent which (i) enhances penetration and transporting of agent (a)

through the tissue surrounding the various cellular elements, generally known as scar tissue or fibrous reaction around the cancerous tumor, and (ii) alters the penetration characteristics of the tissue surrounding the tumor to permit agent (a) to be transported to the center of the tumor, and subjecting the cancer cells to hyperthermia (thermotherapy) therapy. In some instances other modalities (for example chemotherapy and/or radiation therapy) may also be employed.

The glucose inhibiting (non-toxic) amount of the agent that blocks the glucose transport protein of a cell from transporting glucose into the cell (in cancer cells there appear to be more than in normal cells) may comprise:

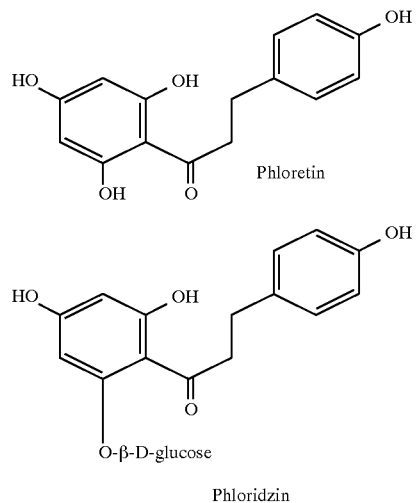

or their analogues including phlorizin glucuronide; 4-deoxy-phloretin-2-D-glucoside and the like.

The effective (non-toxic) amount of the agent which (i) enhances penetration and transport of agent (a) through the tissue surrounding the various cellular elements generally known as scar tissue or fibrous reaction around the cancerous tumor, and (ii) alters the penetration characteristics of the tissue surrounding the tumor to permit agent (a) to be transported to the center of the tumor may comprise dimethyl sulfoxide (DMSO), methylsulfonylmethane (MSM) (also called methylsulfone methane) or other carrier transport-type molecules having the characteristics which (i) enhances penetration and transport of agent (a) through the tissue surrounding the various cellular elements, generally known as scar tissue or fibrous reaction around the cancerous tumor, and (ii) alters the penetration characteristics of the tissue surrounding the tumor to permit agent (a) to be transported to the center of the tumor.

In the publication *Ontario Medicine*, Volume 8, No. 16 dated Aug. 21, 1989 the article "Toxic drug tamed but still potent" describes how an experimental liposomal drug delivery system, is used to encapsulate a highly toxic but highly effective anti-fungal agent, demonstrating that noxious drugs can be transformed into non-toxic agents without compromising clinical efficacy.

The article concluded as follows:

"It was initially hoped that liposomes would offer considerable potential as a drug delivery system for almost all pharmaceutical agents. However, research into the drug delivery system over the past two decades has shown that the artificial, cell-sized spheres form spontaneously with only a small subset of drugs available today thus limiting their use."

The effects of ascorbic acid (Vitamin C) was previously studied in respect of the health of patients. The effects of Vitamin C have also been studied with respect to cancer treatment. It was found that the use of ascorbic acid in 10 gram doses to treat cancer patients increased the survival of terminally ill cancer patients. The use of ascorbic acid was found safe in very high doses.

When the vitamin cannot be absorbed completely from the gastrointestinal system, it will remain water in the bowel leading to diarrhea, which is watery but not dangerous unless it causes dehydration; it quickly forces patients to decrease the doses. It has and is being used by millions of people in these doses. Patients have taken 30 grams per day for 30 years. It is safer than common table salt, gram for gram. It does not cause kidney stones, does not cause pernicious anemia, does not make women infertile, does not cause cancer.

It is therefore an object of this invention to provide formulations suitable for use to treat disease and conditions, the use of such formulations to treat disease and conditions, methods of treating disease and conditions and the delivery of medicinal and therapeutic agents for the treatment of disease (for example, cancer) and conditions.

Further and other objects of the invention will be realized by those skilled in the art from the following disclosure and in which Applicants refer to literature uncovered after the date of their invention.

Hyaluronic acid is a naturally occurring glycosaminoglucan. Its molecular weight may vary from 50,000 dalton upwards, and it forms highly viscous solutions. As regards the actual molecular weight of hyaluronic acid in natural biological contexts, this is still a matter of much uncertainty: When the molecular weight of hyaluronic acid is to be determined, different values are obtained depending on the assay method employed, and on the source, the isolation method etc. The acid occurs in animal tissue, e.g. spinal fluid, ocular fluid, synovial fluid, cockscombs, skin, and also in some streptococci. Various grades of hyaluronic acid have been obtained. A preparation with an allegedly high degree of purity and alleged to be entirely free from side effects, is a non-inflammatory form described in U.S. Pat. No. 4,141,973; this preparation is said to have a molecular weight exceeding 750,000 dalton, preferably exceeding 1,200,000 dalton and is suggested for therapeutic use in various articular conditions.

U.S. Pat. No. 4,801,619 relates to hyaluronic acid administered intra-articularly having a molecular weight of about $3 \times 10^6$ dalton or more, which is prone to decrease the proteoglycan content of synovial fluid to almost normal levels. According to this patent, this indicates a positive effect on the proteoglycan metabolism of a joint. According to the Patent this is applicable both to inflammatory conditions and to degeneration caused by treatment with symptomatics, such as corticosteroid preparations. It is thus clear that a sufficiently high molecular weight of the hyaluronic acid is alleged to counteract side effects that might be caused by corticosteroids or other symptomatics producing similar effects. When corticosteroids are applied, the amount of hyaluronic acid in the synovial cavity will according to the Patent increase substantially and according to the inventors their hyaluronic acid preparations have a very positive effect on such clinical symptoms as pain, swelling and lameness.

The patent states that the objectives of the invention are attained by intra-articular administration of an effective amount of hyaluronic acid with a mean molecular weight exceeding $3 \times 10^6$ dalton, preferably exceeding $4 \times 10^6$ dalton; usually the molecular weight will not exceed $7 \times 10^6$ dalton. The dosage of hyaluronic acid administered is stated to be preferably within the range of 5 mg–80 mg. The amount of solution given at each administration is generally less than 60 ml, e.g. less that 20 ml, of an aqueous solution of the acid or its salt. It is convenient to administer the acid dissolved in water (<2% w/w, buffered to physiological pH), for instance in the form of a water-soluble sodium salt. The exact amount will depend on the particular joint to be treated.

The Merck Index Specifies that Hyaluronic Acid has a Molecular Weight within the range pf 50,000 to $8 \times 10^6$ depending on source, methods of preparation and methods of determination. The Merck Publication teaches hyaluronic acid as a surgical aid (ophthalmological).

U.S. Pat. No. 4,808,576 purports to teach that hyaluronic acid, an agent well known to reduce the sequelae of trauma in mammalian joint tissue when applied directly to the traumatized tissue, will be carried to such traumatized tissue by the mammal's natural processes if applied at a site remote from the traumatized tissue. Thus hyaluronic acid in any therapeutically acceptable form can, according to the Patent, be administered by the typical remote routes including intravenous, intramuscular, subcutaneous and topical.

This, the patent alleges, makes the utilization of hyaluronic acid much more convenient and attractive. For instance the treatment of arthritis in horse or human joints with hyaluronic acid according to the patent no longer requires more difficult intra articular injections.

U.S. Pat. No. 4,725,585relates to a method of enhancing or regulating the host defence of a mammal, said method comprising administering to a mammal a therapeutically effective amount of hyaluronic acid.

At column 1 lines 43–46, the patent provides that the invention was based on the unexpected discovery that administration of hyaluronic acid to mammals results in a considerable increase in the defence.

The hyaluronic acid employed in the Patent was Healon (T. M.) provided by Pharmacia AB, Uppsala, Sweden (Pharmacia AB is entitled to the benefit of U.S. Pat. No. 4,141,973) The patent provides at column 4, line 19 that because a patient's infections had been hard to treat, instead of just hyaluronic acid being administered to the patient to increase the patient's defence, the patient was given hyaluronic acid and an antibiotic. While the patent states that the antibiotic was given in combination with hyaluronic acid, in fact because the hyaluronic acid was administered subcutaneously and because the patient was a heart patient, one skilled in the art would understand that any antibiotic administered, while possibly administered simultaneously was definitely administered separately intravenously (probably) or intramuscularly (less probably). Thus, (most probably) the hyaluronic acid administered according to the teachings of this patent was administered in order to prevent possible development of infections (increase the host's defence) and not for any other reason.

U.S. Pat. No. 4,636,524 discloses cross-linked gels of hyaluronic acid, alone and mixed with other hydrophilic polymers and containing various substances or covalently bonded low molecular weight substances and processes for preparing them. These products are alleged to be useful in numerous applications including cosmetic formulations and as drug delivery systems.

The patent further states that as hyaluronic acid is known to be a biologically tolerable polymer in the sense that it does not cause any immune or other kind of response when introduced into a human body, the cross-linked hyaluronic acid gels can be used for various medical applications. The cross-linked gels modified with other polymers or low molecular weight substances it is alleged can be used as drug delivery devices. For example, the inventors are alleged to have found that heparin introduced in a cross-linked hyaluronic acid gel retained its antithrombogenic activity.

The inventors also allege that they have also found that cross-linked gels of hyaluronic acid can slow down the release of a low molecular weight substance dispersed therein but not covalently attached to the gel macromolecular matrix.

U.S. Pat. No. 4,736,024 purports to teach new medicaments for topical use containing:

(i) an active pharmacological substance or a mixture of pharmacological substances, either active or suitable for topical administration and (ii) a topical vehicle which comprises hyaluronic acid or a molecular fraction of hyaluronic acid or a salt of the same with an alkaline metal, an alkaline earth metal, magnesium, aluminium, ammonium or a pharmacological substance, optionally together with additional conventional excipients for pharmaceutical preparations for topical use.

Applicants are also aware of recently published Japanese Patent Document 61000017 dated 86/01/06 whose English abstract of disclosure states that the Japanese Patent Document relates to the use of hyaluronic acid or cross-linked hyaluronic acid or their salts as the active ingredient for inhibiting carcinoma metastasis.

According to the purported abstract of the Patent more that 1.0% of hyaluronic acid is dissolved in alkaline aq. soln. and pref. more than 50% of $H_2O$ sol. org. solvent. eq. alcohol, acetone, dioxane, against total soln. is added. Preferably the pH is 12–14. Then multifunctional epoxy cpd. is added and reacted at 10–60 deg. C., pref. at 20–40-deg. C. for 24 hrs. Cross-linking ratio of crosslinked hyaluronic acid or its salt is regulated by changing mol ratio of hyaluronic acid or its salt and multifunctional epoxy cpd.. Pref. hyaluronic acid used has intrinsic viscosity 0.2–30,m.w. 4000–2000000. The hyaluronic acid is allegedly used in several dosage forms. Clinical dose for adult is alleged to be normally, as hyaluronic acid or cross-linked hyaluronic acid, 25 mg–5 g/day (p.o.) and 10 mg–2.5 g/l dose (inj). The abstract alleges that the advantage is that the hyaluronic acid has no side effects as other anticancer drugs and has an analgesic and a tissue restoration effect.

European Patent Application 0295092 purports to teach a vehicle together with fragments of hyaluronic acid for delivering of the fragments of hyaluronic acid into the skin to reach the dermal layer of the skin to increase the development of blood vessels for stimulating hair growth or regrowth. The preferred fragments of hyaluronic acid are polysaccharides containing from 7 to 25 monosaccharide units. The patent provides it is apparent that the larger the fragments of hyaluronic acid, the greater the difficulty there is in delivering the fragments to the dermal layer of the skin, unless there is also present in the composition a means for enhancing the activity of said fragments.

The combination may thus include a means for enhancing the activity of the fragments of hyaluronic acid especially to improve their penetration through the skin following topical application. Some activity enhancers, it is alleged, also function as vehicles for the fragments of the hyaluronic acid.

Some activity enhancers are also alleged to possess the ability to stimulate or increase hair growth. Minoxidil is asserted among others to be such an activity enhancer. Thus both the fragments of hyaluronic acid and minoxidil are alleged to stimulate hair growth both delivered by a vehicle.

European Patent Application 0179442 asserts that where free radicals are formed in considerable quantities, hyaluronic acid is broken down or degraded before the hyaluronic acid has given the desired effect.

Canadian Letters Patent 1,240,929 teaches the combination of chondroitin sulfate compound and a hyaluronate to protect both human and animal cell layers and tissue subject to exposure to trauma.

European Patent Application 0208623 purports to teach hyaluronic acid as une augmentation de l'activite de certaines proteases. It also purports to teach the use of hyaluronic acid for treating connective tissue diseases including malignant tumors and cardiovascular disorders.

European Patent Application 270317 purports to teach the combination of an antiviral agent lacking inhibitory action and a compound [for example, hyaluronic acid] possessing cell fusion inhibitory activity and/or virus-adsorption inhibitory activity for treating disease carried by a virus.

U.S. Pat. No. 4,840,941 purports to teach the use of an effective amount of hyaluronic acid as the active agent for the treatment of retroviruses in association with a pharmaceutically acceptable carrier, diluent or excipient.

U.S. Pat. No. 4,851,521 and European Patent Application 0265116 both describe hyaluronic acid fractions, the making thereof and cross-linked esters of hyaluronic. U.S. Pat. No. 4,851,521 describes esters of hyaluronic acid incorporated into pharmaceutical preparations as the active ingredient and as vehicles for ophthamologicell medicines for topical use (See column 11, lines 35 to 42; and column 12, lines 62 to column 13, line 3) and in suppositories for a systemic effect due to the effect of transcutaneous absorption, such as in suppositories.

> The patent provides at column 13, lines 5 to 31: "The vehicling action of the hyaluronic esters also applies to associated medicaments of the type mentioned above in which the active substance acts not only topically or by nasal or rectal absorption, for example by nasal sprays or preparations for inhalation for the oral cavity or the pharynx, but also by oral or parenteral route, for example by intramuscular, subcutaneaous or intravenous route, as it favors absorption of the drug into the application site. The new medicaments can therefore be applied, apart from in the fields already mentioned, in practically all sectors of medicine, such as internal medicine, for example in pathologies of the cardiovascular system, in infections of the respiratory system, the digestive system, the renal system, in diseases of an endocrinological nature, in oncology, in psychiatry etc., and may also be classified therefore from the point of view of their specific action, being perhaps anesthetics, analgesics, anti inflammatories, wound healers, antimicrobics, adrenergic agonsits and antagonists, cytostatics, antirheumatics, antihypertensives, diuretics, sexual hormones, immunostimulants and immunosuppressants, for example, one of the drugs having the activity already described for the therapeutically active alcohols to be used as esterifying component according to the present invention, or for the therapeutically active bases used for the salification of the free carboxylic groups."

Furosemide inhibits sodium reabsorption in the ascending limb of Henle's Loop and in both proximal and distal tubules. The action of the drug is independent of any inhibitory affect on carbonic anhydrase or aldosterone. Furosemide is known to promote diuresis in cases which have previously proved resistant to other diuretics. It has no significant pharmacological effects other than on renal function. In the human it is absorbed from the gastrointestinal tract. Following intravenous administration a diuresis generally occurs within 30 minutes and the duration of action is about 2 hours.

Under a variety of circumstances, the patient can become relatively resistant to the effects of Lasix. This can be so for a variety of reasons but is certainly seen in those situations where there is a major amount of peripheral edema or "third spacing" of fluid which may be true in malnutrition and/or advanced carcinomas. In the latter instances, there is a markedly decreased level of albumin and in all probability, increased permeability and transudation of fluid out of the vascular system. Hence, these patients can become relatively resistant to any of the diuretics including high doses of Lasix administered intravenously.

There have been extensive studies to determine the defect in immune function that allows a tumor cell to develop. It was postulated that the immune system's major role was that of immunological surveillance to destroy abnormal cells. The concept of surveillance, while somewhat simplistic, remains an accepted concept for the elaborate mechanism of immune recognition and function that is present in the higher species—mammals.

It has then been postulated that tumors develop because of local or generalized immune suppression. However, as pointed out by Moller, if general immune suppression occurs, it is only certain types of neoplastic disorders that develop, mainly those of the lympho-reticular system. This observation is correct and represents a major challenge to the immune surveillance theory unless a specific reason can be shown as to why the individual cancer cell can develop plus individually evade the immune system.

It was demonstrated experimentally in 1974 that defects of macrophage function may exist in neoplastic disease.

The initial experiments found suppressor cells to be part of the immune system; these were either of the T-cell type or of the macrophage cell system. There was presence demonstrated in neoplasia, chronic bacterial infection, recovery from massive injury and chronic fungal infection.

There has been repeated demonstration in experimental animals, that the macrophage cell function is altered in neoplastic disease. The macrophages in the animal's systems appeared "blocked" in their function. Generally when removed from the in vivo situation, washed in saline and cultured, they could perform normally. This block has been shown to be related to the excessive production of prostaglandin by neoplastic tissue or by the macrophage itself.

In the basic research efforts in the latter '70s and the early 80's, there existed considerable confusion as to what role immunotherapy should take in cancer. Activation or "hyping" of macrophages was thought to be important. However, in an examination by Romans and Falk of peritoneal macrophages obtained from patients with neoplastic disease, there was definite evidence that these macrophages were already activated yet were co-existing with cancer cells and not causing their destruction.

In this year, 1989 it has been shown that the malfunction of macrophages or the putative block is due to excessive prostaglandin and that this can be altered in tissue culture by corticosteroids, ASA, and the non-steroidal anti-inflammatory drugs, i.e. indomethacin, and naproxen (Naprosyn™). Again, in animal tumors it was repeatedly demonstrated that these substances could alter the response to neoplastic cells and that various combinations of these substances employed with immune enhancing agents could produce very credible success in eliminating experimental tumors. Researchers combined Indomethacin therapy with Interleukin 2 and showed that this could effect a cure with experiment neoplasm.

There were continued problems with the use of any of these agents in the actual human in vivo experience. All of the non-steroidal anti-inflammatory agents (NSAID) produced major toxicity in terms of gastro-intestinal, neurological, and other areas. Thus, the basis of the present approach is that under general circumstances the use of these agents in human disease, in sufficient amounts, the drug will penetrate to any pathological tissue to alter therapeutically local prostaglandin production. While intravenous preparations exist of Indomethacin and now of other agents, the data is overwhelming, as is our own experience, that using these drugs alone produces prohibitive side effects in human subjects. Therefore only insufficient amounts can be brought into the body to effect more than occasional responses in neoplasm.

However the majority of the evidence is present to indicate and therefore it can be postulated that the basis for neoplastic development and how the initial cell "sneaks by" the immune surveillance mechanism relates to its production of prostaglandin. One need postulate only one mutation to alter the amount of prostaglandin synthesis produced by cells when they become "malignant" to establish a mechanism of blocking out the initial cell in any immune reaction, i.e. the macrophage. It therefore became essential to develop a combination of NSAIDS for clinical use to produce a major improvement in response in neoplastic disease and other conditions where excessive prostaglandin synthesis represents the basis of the pathogenesis of this disease state, i.e. arthritis, and various others of the so-called connective tissue inflammatory disorders and/or auto-aggressive diseases.

U.S. Pat. No. 4,711,780 teaches a pharmaceutical composition comprising Vitamin C, a zinc salt:, a sulfur amino acid for treating surface epithelium for epithelium regeneration. Hyaluronic acid may be added for applications in the reproductive tract.

Japanese Patent Publication 63/045223 relates to the treatment of disease caused by retroviruses. Hyaluronic acid is taught for prevention or therapy of leukemia or AIDS by suppressing replication of the virus.

An article entitled *"Inactivation of Herpes Simplex Viruses by Nonionic Surfactants"* by one of the inventors herein (Dr. Samuel Asculai) among others [published in *Antimicrobial Agents and Chemotherapy*, April 1978, pp.686–690] disclosed nonionic surface-active agents, for example nonoxynol-9 found in Delfen™, "possessing ether or amide linkages between the hydrophilic and hydrophobic portions of the molecule rapidly inactivated the infectivity of herpes simplex viruses. The activity stemmed from the ability of nonionic surfactants to dissolve lipid-containing membranes. This was confirmed by observing surfactant destruction of mammalian cell plasma membranes and herpes simplex virus envelopes. Proprietary vaginal contraceptive formulations containing nonionic surfactants also inactivated herpes simplex virus infectivity. This observation suggests that nonionic surfactants in appropriate formulation could effectively prevent herpes simplex virus transmission."

BRIEF DESCRIPTION OF THE FIGURE

FIG. 1 is a graph showing enhanced antibiotic activity of gentamicin when administered together with hyaluronic acid.

SUMMARY OF THE INVENTION

Applicants have now discovered that combinations and formulations (for example an injectable formulation) can be provided for administration to a mammal for the treatment of a disease or condition, which combinations or formulations employ or incorporate as the case may be a therapeutically effective non-toxic amount of a medicinal and/or therapeutic agent to treat the disease or condition (for example a free radical scavenger (for example ascorbic acid (Vitamin C)), Vitamin C (for the treatment of mononucleosis), an anti-cancer agent, chemotherapeutic agent, anti-viral agents for example a nonionic surfactant, e.g. nonoxynol-9 [nonylphenoxy polyethoxy ethanol] found in Delfen™ contraceptive cream, and anionic surfactants (e.g. cetyl pyridinium chloride) and cationic surfactants (e.g. benzalkonium chloride), non-steroidal anti-inflammatory drugs (NSAID) for example indomethacin, naproxen and (+/−) tromethamine salt of ketorolac (sold under the trademark Toradol™) and steroidal anti-inflammatory drugs, anti-fungal agent, detoxifying agents (for example for administration rectally in an enema), analgesic, bronchodilator, anti-bacterial agent, antibiotics, drugs for the treatment of vascular ischemia (for example diabetes and Berger's disease), anti-body monoclonal agent, minoxidil for topical application for hair growth, diuretics (for example furosemide (sold under the trademark Lasix™)), immunosuppressants (for example cyclosporins), lymphokynes (such as interleukin-2 and the like), alpha-and-β-interferon and the like administered with, or carried in, an amount of hyaluronic acid and/or salts thereof (for example the sodium salt) and/or homologues, analogues, derivatives, complexes, esters, fragments, and/or sub units of hyaluronic acid (preferably hyaluronic acid and salts thereof) sufficient to facilitate the agent's penetration through the tissue (including scar tissue), at the site to be treated through the cell membranes into the individual cells to be treated. When such combinations and formulations are administered to patients suffering from the disease or condition, the disease or condition is unexpectedly improved.

The formulation can be administered among other methods, intravenously, intra arterially, intraperitoneally, intrapleurally, transdermally, on the skin (topically), rectally, orally or by direct injection (for example into a tumor, into an abscess or similar disease focus) or put on a patch to be secured to the skin of the patient. The hyaluronic acid and/or salts thereof and the agent can be administered separately but are administered in sufficient amounts and in an immediate time sequence or interval (preferably concurrently and more preferably simultaneously), preferably at the identical site (e.g. one given intravenously and the other "piggy backed"), to treat the disease or condition.

Thus according to an aspect of the invention, a combination is provided suitable for use to treat a condition or disease, the combination comprising therapeutically effective non toxic amounts of (a) a medicinal and/or therapeutic agent to treat a disease or condition (for example a free radical scavenger (for example ascorbic acid (Vitamin C)), Vitamin C (for the treatment of mononucleosis), an anti-cancer agent, chemotherapeutic agent, anti-viral agents for example a nonionic surfactant, e.g. nonoxynol-9 [nonylphenoxy polyethoxy ethanol] found in Delfen™ contraceptive cream, and anionic surfactants (e.g. cetyl pyridinium chloride) and cationic surfactants (e.g. benzalkonium chloride), non-steroidal anti-inflammatory drugs (NSAID) for example indomethacin, naproxen and (+/−) tromethamine salt of ketorolac (sold under the trademark Toradol™) and steroidal anti-inflammatory drugs for example *), anti-fungal agent, detoxifying agents (for example for administration rectally in an enema), analgesic, bronchodilator, anti-bacterial agent, antibiotics, drugs for the treatment of vascular ischemia (for example diabetes and Berger's disease), anti-body monoclonal agent, minoxidil for topical application for hair growth, diuretics (for example furosemide (sold under the trademark Lasix™)), immunosuppressants (for example cyclosporins), lymphokynes (such as interleukin-2 and the like), alpha-and-β-interferon and the like) and (b) a sufficient amount of hyaluronic acid and/or salts thereof (for example sodium salt) and/or homologues, analogues, derivatives, complexes, esters, fragments, and/or subunits of hyaluronic acid, preferably hyaluronic acid and salts thereof, sufficient to facilitate the agent's penetration through the tissue (including scar tissue) at the site to be treated through the cell membranes into the individual cells to be treated.

The combination can be administered separately or as a mixture or solution. If administered separately the components are preferably administered simultaneously and at the identical site.

According to another aspect of the invention, a formulation is provided suitable for use to treat a condition or disease, the formulation comprising a therapeutically effective non-toxic amount of a medicinal and/or therapeutic agent to treat a disease or condition (for example a free radical scavenger (for example a free radical scavenger (for example ascorbic acid (Vitamin C)), Vitamin C (for the treatment of mononucleosis), an anti-cancer agent, chemotherapeutic agent, anti-viral agents for example a nonionic surfactant, e.g. nonoxynol-9 [nonylphenoxy polyethoxy ethanol] found in Delfen™ contraceptive cream, and anionic surfactants (e.g. cetyl pyridinium chloride) and cationic surfactants (e.g. benzalkonium chloride), non-steroidal anti-inflammatory drugs (NSAID) for example indomethacin, naproxen and (+/−) tromethamine salt of ketorolac (sold under the trademark Toradol™) and steroidal anti-inflammatory drugs, anti-fungal agent, detoxifying agents (for example for administration rectally in an enema), analgesic, bronchodilator, anti-bacterial agent, antibiotics, drugs for the treatment of vascular ischemia (for example diabetes and Berger's disease), anti-body monoclonal agent, minoxidil for topical application for hair growth, diuretics (for example furosemide (sold under the trademark Lasix™)), immunosuppressants (for example cyclosporins), lymphokynes (such as interleukin-2 and the like), alpha-and-β-interferon and the like), in an amount of hyaluronic acid and/or salts thereof (for example the sodium salt) and/or homologues, analogues, derivatives, complexes, esters, fragments and sub units of hyaluronic acid, preferably hyaluronic acid and salts thereof, sufficient to facilitate the agent at the site to be treated, to penetrate through the tissue (including scar tissue) through cell membranes into the individual cells to be treated.

According to another aspect of the invention a method of treating a condition or a disease in a mammal is provided comprising administering to the mammal, a combination of a therapeutically effective non-toxic amount of (a) a medicinal and/or therapeutic agent to treat a disease or condition (for example a free radical scavenger (for example ascorbic acid (Vitamin C)), Vitamin C (for the treatment of mononucleosis), an anti-cancer agent, chemotherapeutic agent, anti-viral agents for example a nonionic surfactant, e.g. nonoxynol-9 [nonylphenoxy polyethoxy ethanol] found in Delfen™ contraceptive cream, and anionic surfactants (e.g. cetyl pyridinium chloride) and cationic surfactants (e.g. benzalkonium chloride), non-steroidal anti-inflammatory drugs (NSAID) for example indomethacin, naproxen and (+/−) tromethamine salt of ketorolac (sold under the trademark Toradol™) and steroidal anti-inflammatory drugs, anti-fungal agent, detoxifying agents (for example for administration rectally in an enema), analgesic, bronchodilator, anti-bacterial agent, antibiotics, drugs for the treatment of vascular ischemia (for example diabetes and Berger's disease), anti-body monoclonal agent, minoxidil for topical application for hair growth, diuretics (for example furosemide (sold under the trademark Lasix™), immunosuppressants (for example cyclosporins), lymphokynes (such as interleukin-2 and the like), alpha-and-β-interferon and the like) and (b) a sufficient amount of hyaluronic acid and/or salts thereof (for example sodium salt) and/or homologues, analogues, derivatives, complexes, esters, fragments, and/or sub units of hyaluronic acid, preferably hyaluronic acid and salts thereof sufficient to facilitate the agent at the site to be treated to penetrate through the tissue (including scar tissue), through the cell membranes into the individual cells to be treated.

Preferably (a) and (b) are administered simultaneously at the identical site, for example, one intravenously and the other "piggy backed".

According to another aspect of the invention a method of treating disease or a condition is provided comprising administering to a mammal a therapeutically effective non toxic amount of a formulation comprising a therapeutically effective amount of a medicinal and/or therapeutic agent to treat a disease or condition (for example a vitamin (for example a free radical scavenger (for example ascorbic acid (Vitamin C)), Vitamin C (for the treatment of mononucleosis), an anti-cancer agent, chemotherapeutic agent, anti-viral agents for example a nonionic surfactant, e.g. nonoxynol-9 [nonylphenoxy polyethoxy ethanol] found in Delfen™ contraceptive cream, and anionic surfactants (e.g. cetyl pyridinium chloride) and cationic surfactants (e.g. benzalkonium chloride), non-steroidal anti-inflammatory drugs (NSAID) for example indomethacin, naproxen and (+/−) tromethamine salt of ketorolac (sold under the trademark Toradol™) and steroidal anti-inflammatory drugs, anti-fungal agent, detoxifying agents (for example for administration rectally in an enema), analgesic, bronchodilator, anti-bacterial agent, antibiotics, drugs for the treatment of vascular ischemia (for example diabetes and Berger's disease), anti-body monoclonal agent, minoxidil for topical application for hair growth, diuretics (for example furosemide (sold under the trademark Lasix™)), immunosuppressants (for example cyclosporins), lymphokynes (such as interleukin-2 and the like), alpha-and-β-interferon and the like in an amount of hyaluronic acid and/or salts thereof (for example the sodium salt) and/or homologues, analogues, derivatives, complexes, esters, fragments and/or sub units of hyaluronic acid, preferably hyaluronic acid and salts thereof, sufficient to facilitate the agent at the site to be treated to penetrate through the tissue (including scar tissue) through cell membranes into the individual cells to be treated.

According to another aspect of the invention, delivery of a therapeutically effective amount of a medicinal and/or therapeutic agent to treat a disease or condition in a mammal is provided, the delivery comprising administering a therapeutically effective non toxic amount of a medicinal and/or therapeutic agent (for example a free radical scavenger (for example ascorbic acid (Vitamin C)), Vitamin C (for the treatment of mononucleosis), an anti-cancer agent, chemotherapeutic agent, anti-viral agents for example a nonionic surfactant, e.g. nonoxynol-9 [nonylphenoxy polyethoxy ethanol] found in Delfen™ contraceptive cream, and anionic surfactants (e.g. cetyl pyridinium chloride) and cationic surfactants (e.g. benzalkonium chloride), non-steroidal anti-inflammatory drugs (NSAID) for example indomethacin, naproxen and (+/-) tromethamine salt of ketorolac (sold under the trademark Toradol™) and steroidal anti-inflammatory drugs, anti-fungal agent, detoxifying agents (for example for administration rectally in an enema), analgesic, bronchodilator, anti-bacterial agent, antibiotics, drugs for the treatment of vascular ischemia (for example diabetes and Berger's disease), anti-body monoclonal agent, minoxidil for topical application for hair growth, diuretics (for example furosemide (sold under the trademark Lasix™)), immunosuppressants (for example cyclosporins), lymphokynes (such as interleukin-2 and the like), alpha-and-β-interferon and the like with a sufficient amount of hyaluronic acid and/or salts thereof and/or homologues, analogues, derivatives, complexes, esters, fragments, and sub units of hyaluronic acid, preferably hyaluronic acid and salts thereof, sufficient to transport or facilitate the transport of, the agent to the site to be treated through the cell membranes into the individual cells to be treated.

Thus according to another aspect of the invention, use of a combination or formulation is provided to treat a disease or condition, the combination and formulation comprising a therapeutically effective non-toxic amount of a medicinal and/or therapeutic agent to treat a disease or condition (for example a vitamin (for example a free radical scavenger (for example ascorbic acid (Vitamin C)), Vitamin C (for the treatment of mononucleosis), an anti-cancer agent, chemotherapeutic agent, anti-viral agents for example a nonionic surfactant, e.g. nonoxynol-9 [nonylphenoxy polyethoxy ethanol] found in Delfen™ contraceptive cream, and anionic surfactants (e.g. cetyl pyridinium chloride) and cationic surfactants (e.g. benzalkonium chloride), non-steroidal anti-inflammatory drugs (NSAID) for example indomethacin, naproxen and (+/-) tromethamine salt of ketorolac (sold under the trademark Toradol™) and steroidal anti-inflammatory drugs, anti-fungal agent, detoxifying agents (for example for administration rectally in an enema), analgesic, bronchodilator, anti-bacterial agent, antibiotics, drugs for the treatment of vascular ischemia (for example diabetes and Berger's disease), anti-body monoclonal agent, minoxidil for topical application for hair growth, diuretics (for example furosemide (sold under the trademark Lasix™)), immunosuppressants (for example cyclosporins), lymphokynes (such as interleukin-2), alpha-and-β-interferon and the like and a sufficient amount of hyaluronic acid and/or salts thereof (for example sodium salt) and/or homologues, analogues, derivatives, complexes, esters, fragments, and/or sub units of hyaluronic acid, preferably hyaluronic acid and salts thereof to facilitate agent transported to the site to be treated, to penetrate through the cell membranes into the individual cells to be treated.

Applicants postulate that the hyaluronic acid and/or salts thereof and/or the homologues, analogues, derivatives, complexes, esters, fragments, and/or sub units of hyaluronic acid facilitate the transport of the agent to the site to be treated and to penetrate the tissue (including scar tissue) through all membranes in the individual cells to be treated.

By way of example and to illustrate the facilitation of the delivery or transport of a chemical to a site in a mammal, when ethyl alcohol is injected directly into a tumor, and sonographic (ultrasound) assessment is made, it is not dispersed throughout the tumor. When the ethyl alcohol to be administered into a tumor is carried by hyaluronic acid and/or salts thereof, sonographic assessment of the tumor, demonstrates the dispersion of the ethyl alcohol throughout the tumor.

While Applicants postulate that the hyaluronic acid facilitates the transport and delivery, Applicants' invention may be used as described irrespective of the actual method of operation of the hyaluronic acid and/or salts thereof and/or the homologues, analogues, derivatives, complexes, esters, fragments and sub units of hyaluronic acid.

The combination of hyaluronic acid and salts thereof and other forms with different chemicals and drugs (Vitamin C, anti-cancer drugs, etc.) alters their distribution and performance in the human body and produces an unusual targeting for underperfused tissue and/or pathological tissue. In this regard the use of ascorbic acid (Vitamin C) as a free radical scavenger (50 gm daily-1000 times the daily dose in therapeutic purposes as a Vitamin) administered intravenously with 300–500 mg of hyaluronic acid (sodium hyaluronate) immediately relieves bone pain and muscle pain and reduces inflammation in cancer patients. The hyaluronic acid enhances the anti-neoplastic activity and effect of the ascorbic acid. It is thought that this enhanced activity eliminates the free radicals by acting as a free radical scavenger. In any event the patients feel better. This is also demonstrated with furosemide and hyaluronic acid where the activity of furosemide is enhanced only minimally when administered with hyaluronic acid to a "normal" subject but the activity is enhanced significantly when administered to a patient whose kidney is underperfused or malfunctioning due to insufficient intra-vascular volume.

A similar situation occurs with the NSAIDS. As a major amount of soluble indomethacin is required, the chemical product was solubilized using n-methyl glucamine at a dilution of 5 mg/ml of n-methyl glucamine (NMG). This substance is then passed through a 22 micron Milipore filter to produce sterility. This material is non-toxic at 16 fold the therapeutic dose in animals and for this reason was considered appropriate to be used in human conditions. Thus, Indocid™ solubilized in NMG is administered to human patients either into the tumor intraperitoneally, intrapleurally, or intravascularly at a varying dose up to 10 mg/kg where each dose of indomethacin is combined with 200–1000 mg of hyaluronic acid (for example "LifeCore™" hyaluronic acid [sodium hyaluronate]) diluted in the original solution of indomethacin and NMG with for example the "LifeCore™" hyaluronic acid. This produces an appropriate mixture and can be administered safely by any of the routes. [Similar clinical studies have been done with hyaluronic acid prepared by other methods, i.e. extraction. The extracted material is satisfactory to use for intratumor, intraperitoneal or intrapleural use with this substance.]

Thus and according to another aspect of the invention when an NSAID for example indomethacin (dissolved in n-methyl glucamine) or other NSAID is administered with greater than 200 mg hyaluronic acid for 1–2 mg/kg body weight of the NSAID (in one instance indomethacin and NMG), no major toxic side effects occur such as gastrointestinal distress, neurological abnormalities, depression, etc., even at elevated amounts of indomethacin (if necessary). If the amount of hyaluronic acid is decreased below that amount, the usual side effects may begin to reoccur. In addition, the responses that have been observed are superior when the NSAID (for example Indocid™) is combined with hyaluronic acid demonstrating clearly that the combination is now "targeting" to the pathological tissue even when administered by the systemic intravenous route. Thus, it has been observed that patients with neoplastic diseases when receiving in addition to other chemicals (for example ascorbic acid [Vitamin C], phloretin and anticancer drugs), 50–200 mg NSAID—hyaluronic acid (sodium hyaluronate) (for example indomethacin and hyaluronic acid) experience dramatic relief of pain immediately. This is followed within a short period of time by a resolution and resorbtion of neoplastic lesions with an improvement of pulmonary, and liver function if there is tumor present in these organs. Thus the dead tumor material and the debris and tumor toxins appear to be better eliminated by the body through the action of the macrophages whose activity is enhanced by the addition of the NSAID (or a steroidal anti-inflammatory drug) administered with hyaluronic acid (or salt or other form thereof). Thus Applicants believe that the addition of the NSAID for example with hyaluronic acid (sodium hyaluronate) deblocks the macrophages by preventing enzymatic production of prostaglandin synthetase which blocks macrophage functioning. Thus the hyaluronic acid (and salt and other forms) not only enhance the activity of the NSAID but also reduce any side effects and toxicity that is associated with the use of the prostaglandin synthesis inhibitors.

Examples of agents suitable for use as chemotherapeutic agents are novantrone (Mitoxantrone), Methotrexate, 5-FU (5-Fluouracil), carboplatinum, methyl CCNU administered orally and Mitomycin C.

In one instance methotrexate has been administered with hyaluronic acid over an area of tumor tissue, (e.g. the chest wall) for a period of 5–7 consecutive days. The patient's hemotological indices were lowered at least comparable to methotrexate being given at the same doses either intravenously or orally.

Further when the cancerous tumor breaks up (after treatment as previously described) in many instances the liver cannot cope with the tumor toxins and debris and residue, killing the patient. Not only is the use of hyaluronic acid with an NSAID appropriate, so is the use of enemas employing hyaluronic acid (sodium hyaluronate) and a detoxifying agent administered into the large bowel.

The hyaluronic acid and salts thereof may be utilized at varying doses—10 to 1000 mg/70 kg person with the optimal doses tending to range between 50 and 350 mg/70 kg individual. As there is no toxicity, the hyaluronic acid can obviously be administered in a dose excess (for example 3000 mg/70 kg individual) without any adverse effects.

Thus, we have combined hyaluronic acid and/or salts thereof with cytotoxic chemotherapeutic agent, for example either administering hyaluronic acid immediately after the agent (if the two cannot be mixed beforehand) or having mixed the two, that is hyaluronic acid and the drug, before administration. We have utilized for example, adriamycin administering adriamycin prior to hyaluronic acid, methotrexate where the two agents are mixed together, mitomycin C, bleomycin, 5-Fluorouracil, novantrone, carbo- and cis-platinum, and in all of these latter instances the drug has been mixed directly with hyaluronic acid at a dose of 10 mg/per ml of the hyaluronic acid increasing the total dose up to 100 mg with the standard dose of the drug in question being utilized.

Previously, we have utilized phloridzin, phloretin, and 5-deoxyglucuronide of phloridzin as agents with dimethyl sulfoxide to competitively block glucose transport in neoplastic cells. These agents can also be combined with hyaluronic acid at similar doses to those already mentioned for chemotherapeutic drugs where phloretin is solubilized for example by the agent N-methyl glucamine.

Thus, a treatment protocol in various different neoplastic situations may consist of the administration of Ascorbic Acid and Oncostatin IV, a combination of phloretin, solubilized in N methyl glucamine, with a mixture of hyaluronic acid or salt thereof using a dose of 2 to 4 grams of phloretin solubilized as described with 30 mg to 1000 mgs or more (dose excess) of hyaluronic acid or sodium salt. This has allowed substantially enhanced penetration of the drug into tumor cells and has effected a much better result when these tumors are deprived of glucose and then subsequently stressed either by hyperthermia, chemotherapy and/or radiation. Similarly, cytotoxic chemotherapeutic agents already mentioned have been combined with comparable doses of hyaluronic acid and and/or salts thereof administered either intravenously, intra-arterially, intraperitoneally or intrapleurally or directly into the tumor by injection through a needle placed under sonographic or CT guidance.

Intradermal delivery of other drugs may also be accomplished with hyaluronic acid and/or salts thereof: for example insulin in diabetes, estrogen in post-menopausal women, progestegens in control of fertility and anti-metabolites for the prevention of topical infection such as those caused by coryne bacterium acnes. They may also be applied using hyaluronic acid.

Intravenous administration of bronchodilators may also (for example aminophylline and theophylline) may also be accomplished with hyaluronic acid and/or salts thereof.

Enhancement of the effect of the bronchodilators by administration with hyaluronic acid has been the result. Oral administration with hyaluronic acid and/or salt may also be suitable.

According to another aspect of the invention, the combination of a non-ionic surfactant for example nonoxynol-9 [nonylphenoxy polyethoxy ethanol] [found in Delfen (t.m.) contraceptive cream] and hyaluronic acid and/or salts thereof and other forms is provided for treating:

(a) herpes simplex type I and type II (b) herpes zoster (shingles)

and unexpectedly provide immediate relief of symptoms and subsequent disappearance of lesions.

The non-ionic surfactant preferably comprises an ether or an amide linkage between the hydrophilic and hydrophobic portions of the molecule, being more active than the surfactants having an ester- or an ether-ester linkage.

The following nonionic surfactants and identified linkages are offered for consideration.

| Surfactant | Linkage |
| --- | --- |
| None (control virus) | |
| 5% Nonoxynol-9 (nonylphenoxy-polyethoxy ethanol) | Ether |
| 1% Triton X-100 (p-diisobutylphenoxy-polyethyoxy-ethanol) | Ether |
| 1% Brij-97 (polyoxyethylene (10) oleyl ether) | Ether |
| 1% Span-20 (sorbitran monclamate) | Ester |
| 1% Span-80 (sorbitan moncleate) | Ester |
| 1% Tween-20 (polysorbate 20) | Ether-ester |
| 1% Tween-80 (polysorbate 80) | Ether-ester |
| 1% Onyxol 345 | Amide |

Where foreign objects (for example drainage tubes) must be implanted into a human body and be left for use, it is imperative that the tissue surrounding the implant not become infected because once the tissue becomes infected, usually no matter how much antibiotic is administered the infection does not clear and the implant must be removed. Applicants have found however that where the infected tissue surrounding the implant is treated with the antibiotic carried in hyaluronic acid (sodium hyaluronate), the infection rapidly clears and the implant need not be removed.

Applicants have also found that in respect of treating vascular ischemia (for example in cancer patients where the tumor tissue is under perfused, in patients suffering from diabetes and Berger's disease), the administration of the medicines in hyaluronic acid (sodium hyaluronate) enhances the patient's response to the drug.

In patients suffering from brain tumors, the swelling must be reduced. Administration of dimethyl sulfoxide (DMSO) in amounts of less than 100 gm daily in a 10% solution in hyaluronic acid (sodium hyaluronate) –300–500 mg reduces acute brain and spinal edema.

For the treatment of mononucleosis, Applicants have successfully administered to a patient suffering from a particularly bad case for some time, Vitamin C and hyaluronic acid and the patient rapidly recovered.

One form of hyaluronic acid and/or salts thereof (for example sodium salt) and homologues, analogues, derivatives, complexes, esters, fragments, and sub units of hyaluronic acid, preferably hyaluronic acid and salts and thereof suitable for use with Applicant's invention is a fraction supplied by Sterivet Laboratories Limited. One such fraction is a 15 ml vial of Sodium hyaluronate 20 mg/ml (300 mg/vial-Lot 2F3). The sodium hyaluronate fraction is a 2% solution with a mean average molecular weight of about 225,000. The fraction also contains water q.s. which is triple distilled and sterile in accordance with the U.S.P. for injection formulations. The vials of hyaluronic acid and/or salts thereof may be carried in a Type 1 borosilicate glass vial closed by a butyl stopper which does not react with the contents of the vial.

The fraction of hyaluronic acid and/or salts thereof (for example sodium salt) and homologues, analogues, derivatives, complexes, esters, fragments, and sub units of hyaluronic acid, preferably hyaluronic acid and salts thereof may comprise hyaluronic acid and/or salts thereof having the following characteristics:

a purified, substantially pyrogen-free fraction of hyaluronic acid obtained from a natural source having at least one characteristic selected from the group consisting of the following:

i) a molecular weight within the range of 150,000–225,000;

ii) less than about 1.25% sulphated mucopolysaccharides on a total weight basis;

iii) less than about 0.6% protein on a total weight basis;

iv) less than about 150 ppm iron on a total weight basis;

v) less than about 15 ppm lead on a total weight basis;

vi) less than 0.0025% glucosamine;

vii) less than 0.025% glucuronic acid;

viii) less than 0.025% N-acetylglucosamine;

ix) less than 0.0025% amino acids;

x) a UV extinction coefficient at 257 nm of less than about 0.275;

xi) a UV extinction coefficient at 280 nm of less than about 0.25, and xii) a pH within the range of 7.3–7.9.

Preferably the hyaluronic acid is mixed with water and the fraction of hyaluronic acid fraction has a mean average molecular weight within the range of 150,000–225,000.

More preferably the fraction of hyaluronic acid comprises at least one characteristic selected from the group consisting of the following characteristics:

i) less than about 1% sulphated mucopolysaccharides on a total weight basis;

ii) less than about 0.4% protein on a total weight basis;

iii) less than about 100 ppm iron on a total weight basis;

iv) less than about 10 ppm lead on a total weight basis;

v) less than 0.00166% glucosamine;

vi) less than 0.0166% glucuronic acid;

vii) less than 0.0166% N-acetylglucosamine;

viii) less than 0.00166% amino acids;

x) a UV extinction coefficient at 257 nm of less than about 0.23;

xi) a UV extinction coefficient at 280 nm of less than 0.19; and xii) a pH within the range of 7.5–7.7

Other forms of hyaluronic acid and/or its salts, and homologues, derivatives, complexes, esters, fragments and sub units of hyaluronic acid may be chosen from other suppliers, for example those described in the prior art documents previously referred to. In addition Applicants have successfully employed sodium hyaluronate produced and supplied by LifeCore™ Biomedical, Inc. having the following specifications

| Characteristics | Specification |
| --- | --- |
| Appearance | White to cream colored particles |
| Odor | No perceptible odor |
| Viscosity Average Molecular Weight | <750,000 Daltons |
| UV/Vis Scan, 190–820 nm | Matches reference scan |
| OD, 260 nm | <0.25 OD units |
| Hyaluronidase Sensitivity | Positive response |
| IR Scan | Matches reference |
| pH, 10 mg/g solution | 6.2–7.8 |
| Water | 8% maximum |
| Protein | <0.3 mcg/mg NaHy |
| Acetate | <10.0 mcg/mh NaHy |
| Heavy Metals, maximum ppm | |

| As | Cd | Cr | Co | Cu | Fe | Pb | Hg | Ni |
| --- | --- | --- | --- | --- | --- | --- | --- | --- |
| 2.0 | 5.0 | 5.0 | 10.0 | 10.0 | 25.0 | 10.0 | 10.0 | 5.0 |

| | |
| --- | --- |
| Microbial Bioburden | None observed |
| Endotoxin | <0.07 EU/mg NaHy |
| Biological Safety Testing | Passes Rabbit Ocular Toxicity Test |

The following references teach hyaluronic acid, sources thereof and processes of the manufacture and recovery thereof.

U.S. Pat. No. 4,141,973 teaches hyaluronic acid fractions (including sodium salts) having:

"(a) an average molecular weight greater than about 750,000, preferably greater than about 1,200,000—that is, a limiting viscosity number greater than about 1400 cm$^3$/g., and preferably greater than about 2000 cm$^3$/g.;

(b) a protein content of less than 0.5% by weight;

(c) ultraviolet light absorbance of a 1% solution of sodium hyaluronate of less than 3.0 at 257 nanometers wavelength and less than 2.0 at 280 nanometers wavelength;

(d) a kinematic viscosity of a 1% solution of sodium hyaluronate in physiological buffer greater than about 1000 centistokes, preferably greater than 10,000 centistokes;

(e) a molar optical rotation of a 0.1–0.2% sodium hyaluronate solution in physiological buffer of less than $-11 \times 10^3$ degree-cm$^2$/mole (of disaccharide) measured at 220 nanometers;

(f) no significant cellular infiltration of the vitreous and anterior chamber, no flare in the aqueous humor, no haze or flare in the vitreous and no pathological changes to the cornea, lens,1 iris, retina, and choroid of the owl monkey eye when one milliliter of a 1% solution of sodium hyaluronate dissolved in physiological buffer is implanted in the vitreous replacing approximately one-half the existing liquid vitreous, said HUA being (g) sterile and pyrogen free and (h) non-antigenic."

Canadian Letters Patent 1,205,031 (which refers to U.S. Pat. No. 4,141,973 as prior art) refers to hyaluronic acid fractions having average molecular weights of from 50,000 to 100,000; 250,000 to 350,000; and 500,000 to 730,000 and discusses processes of their manufacture.

Where high molecular weight hyaluronic acid (or salts or other forms thereof) is used, it must be diluted to permit administration and ensure no intramuscular coagulation.

One formulation of Ascorbic Acid (Vitamin C) injection USP is manufactured by Steris Laboratories, Inc., Phoenix, Az., 85043 U.S.A. and comprises 22 mg/ml (equivalent to sodium ascorbate 250 mg/ml) in 30 ml, 50 ml, or 100 ml individual containers, 30 ml size being preferred.

Thus Applicant has combined hyaluronic acid (and sodium hyaluronate and/or other forms) with medicinal and/or therapeutic agents for the treatment of conditions and diseases with totally unexpected results:

For Example

|   | Condition/Disease | Chemicals & Drugs |
|---|---|---|
| 1. | Cancer, increasing activity of macrophages | free radical scavenger, superoxide dismutase, ascorbic acid (Vitamin C) anti-cancer drugs, NSAID, Chemotherapeutic Agents, detoxifying Agents (e.g. cholestyramine) |
| 1A. | Reduction of swelling in brain of person suffering brain trauma | Dimethyl Sulfoxide (DMSO) |
| 2. | Hair growth | minoxidil - combination - grow more hair when applied topically |
| 3. | Herpes, canker sore, shingles | nonionic surfactants, e.g., nonoxynol-9 and anionic, (e.g. cetyl pyridinium chloride) and cationic (e.g. benzalkonium choride), surfactants |
| 4. | Renal failure, cardiac insufficiency, hypertension, edema | diuretics - furosemide |
| 5. | Infection, acne, mononucleosis | antibiotics, antibacterials, antimicrobials, etc., ascorbic acid and hyaluronic acid |
| 6. | Transplants | cyclosporins |
| 7. | Inflammation, elimination of tumor break down material (toxins and debris), decreasing side effects, relief of pain (e.g. back pain) | non-steroidal anti-inflammatories, NSAID e.g. diclofenac, indomethacin, piroxicam, ibuprofen, tromethamine salt of Ketorolac, naproxen, |
| 8. | Detoxification | enema, detoxifying agent, peritoneal dialysis |

-continued

|   | Condition/Disease | Chemicals & Drugs |
|---|---|---|
| 9. | Bronchodilation | bronchodilators, e.g. beclometasone diproprionate (sodium cromoglycate although not specifically a bronchodialator), theophylline |
| 10. | Vascular ischemia | treat limbs in respect of diabetes, Berger's disease, etc. with suitable medicine e.g. Trental |
| 11. | HIV (AIDS) | DMSO, Vitamin C, NSAID (e.g. indomethacin, naproxen, ketorolac tromethamine), interferon, Vibramycin ™, (doxcycline), tetracycline |
| 12. | Diabetes | insulin |
| 13. | Post-menopause | estrogens replacement |
| 14. | Prevention of topical infection | antimetabolites (e.g. sulfonamides) |
| 15. | Reduction of swelling | DMSO |
| 16. | Hypertension, cardiac insufficiency | Calcium channel blockers, e.g. - Nifedipine β-Blockers e.g. atenolol, propranolol |
| 17. | Prostaglandin Synthesis inhilition | acetylsalicylic acid |
| 18. | Enhance oxygenation of tissue by perfusion fluid bathing the tissue (for transplantation purposes | perfusate |

In respect of the treatment of cancer particularly, Applicants have now provided a method of treatment and combinations of chemicals and drugs which appear to enhance a patient's life expectancy and quality of life (even those patients not responding to the usual treatments). Applicants have successfully treated patients with their invention, increasing the rate of tumor destruction, improving for example macrophage function, to enable the body to eliminate the tumor cells, dead tumor waste, debris, and toxins.

EXAMPLES

The following examples are offered to illustrate Applicants' invention. In substantially all, if not all cancer cases, the patient had been unresponsive to conventional treatment. The hyaluronic acid referred to herein also includes other forms—for example sodium hyaluronate.

CASE I:

A 59 year old male with a laryngeal epidermoid (squamous type tumor) treated in its primary state with a combination of surgery and radiation developed metastatic disease in the liver some seven years later. Two major tumors were noted at a size of 12 cm and 6 cm diameter. These were treated with combination therapy using systemic chemotherapy with added DMSO to enhance penetration, phloretin solubilized by N methyl glucamine with added DMSO to enhance penetration and the direct administration of adriamycin, carboplatinum and methotrexate into the tumor by systemic and intratumor injection therapy but in this case but with added hyaluronic acid at a dose of 10 to 60 mgs for the different drugs. This was achieved without any adverse effects and the patient was reassessed four weeks later. At that point in time the smaller tumor had disappeared entirely. The larger tumor was apparent only as a necrotic focus measuring now 5 cm in diameter but no apparent surviving tumor could be detected by examination and needle biopsy. This case illustrates the superior effect of hyaluronic acid on penetration of drug thus allowing better tumor destruction.

Follow-Up

Subsequently patient was given treatment of Indomethacin 300 mg and 300 mg Hyaluronic Acid daily; patient was in remission, however patient died of infection at a later date.

CASE II:

A 42 year old female developed malignant melanoma with tumor present in the left upper thigh and inguinal nodes, the abdominal cavity and liver, lungs, and the base of the brain affecting involvement of various cranial nerves. Her primary tumor had been excised and she had developed recurrent disease which was deemed untreatable as there is no cytotoxic or cytostatic chemotherapy that has major effects on this tumor when it is as widespread as observed in this patient. The patient was treated with a combination of phloretin solubilized in N methyl glucamine with added hyaluronic acid at a dose of 10 to 50 mg/2 to 4 grams administered intravenously and this agent was given for five days over 4–24 hours/day. She also received hyperthermia to the various areas of the tumor and concomitant systemic therapy with carboplatinum with added hyaluronic acid at a dose of 250 mg carboplatinum total plus methyl CCNU administered at a total dose of 120 mg over 5 days orally while the patient received hyaluronic acid systemically. Methotrexate mixed with hyaluronic acid was injected into the tumor which could be palpated in the left thigh or inguinal region at a dose of 37.5 mg with 60 mg of hyaluronic being added, the doses being divided equally at two different days by injection. The patient responded over the next 10 to 20 days with dramatic and total regression of the upper thigh and inguinal tumors, dramatic improvement in liver function with the tumors in the liver becoming cystic (generally regarded as a sign of tumor break down) and disappearance of the lung tumors. The tumor at the base of the brain regressed as manifested by improvement of her cranial nerve function and a decrease of pain and headaches. In this patient a tumor which is unresponsive to the majority of agents at this phase of development was made markedly responsive when the same agents were used with hyaluronic acid as a penetrating agent.

Follow-Up

The patient was subsequently given treatments of phloretin, indomethacin (NSAID) and hyaluronic acid. This patient is now in complete remission.

CASE III:

A 55 year old female patient with cancer of the gallbladder occupying the entire right lobe of the liver. This patient had been treated on three previous occasions with a combination of heat, systemic chemotherapy with added DMSO, phloretin with added DMSO and direct injection of cytotoxic drugs with added DMSO. Beginning May 1989 she was treated with the comparable drugs with added hyaluronic acid as a carrier or dispersing molecule administered both systemically and by direct injection into the tumor. The tumor which had shrunk marginally by approximately 20% prior to this now reduced in size dramatically by over 50% and continues to diminish in size. This tumor is judged unresponsive to these drugs alone when administered by the normal routes.

Follow-Up

Unfortunately the patient relapsed, became depressed and died.

CASE IV:

A 55 year old female with cancer of the colon metastatic to the liver with one major large tumor mass occupying the entire right lobe of the liver and medial segment of the left lobe extending into the 1 left lobe and judged unresectable by a hepatic surgeon two months earlier was treated with systemic chemotherapy and injection of chemotherapeutic agents directly into the tumor plus phloretin solubilized with N methyl glucamine with hyaluronic acid and hyperthermia. The patient had a three day course of therapy and was injected on one occasion directly into the tumor with cytotoxic drugs and hyaluronic acid and reassessed three weeks later. Sonographic examination showed total liquafaction of the tumor leaving only a small rim of apparently viable tissue; 500 ccs of amber colored fluid with necrotic tumor tissue present was drained from the now cystic lesion. This is an unusual and dramatic response for an adenocarcinoma which generally responds extremely slowly. It is judged that less than 30% of these patients achieved any significant disease regression utilizing standard cytotoxic or cytostatic chemotherapy. The enhanced destruction here occurring over three weeks and is judged as due to the use of the carrier penetrating molecule, hyaluronic acid.

Follow-Up

From the examinations, there was total tumor necrosis. The patient however died some time later of liver failure and pulmonary embolism.

CASE V:

A 53 year old man with transitional cell cancer of the bladder in a very advanced state of his disease with metastases involving the entire left pelvis, extending to the periaortic and parapancreatic and supraclavicular nodes having recurred after previous surgical excision, radiation and having not responded by major regression to standard chemotherapy was treated using phloretin solubilized in N-methyl glucamine with added hyaluronic acid with a direct injection of carboplatinum and methotrexate into the tumor tissue. Hyperthermia to the areas of the tumor was also applied. The patient developed a dramatic response and developed a febrile reaction due to tumor break down and release of bacteria. This reaction was controlled by antibiotics and appropriate hydration and as the patient was observed through this phase a dramatic decrease in the size of the tumor was observed on an almost daily basis with an over 50% reduction in tumor size having occurred by 7 days after therapy. This is a remarkable and dramatic response of a tumor which at this phase had been judged as unresponsive to all therapy and it is thought to be due to the use of the drug which blocks glucose transport employed here with a carrier and penetrating molecule, hyaluronic acid and chemotherapy administered directly into the tumor with the same agent.

Follow-Up

There was, as a result, total tumor necrosis. However at a later date, the patient died of an infection.

CASE VI:

This Patient had a right upper lobe lesion diagnosed, confirmed by biopsy and deemed not surgically resectable. This tumor, according to documentation utilizing chemotherapy or radiotherapy has a zero response rate. He was treated with systemic chemotherapy in hyaluronic acid as follows:

| DATE | DRUG | DOSE |
| --- | --- | --- |
| 05/10 | vinblastine | 3 mg |
| 05/10 | mitomycin | 3 mg |
| 05/10 | calcium leukovorin | 40 mg |
| 05/10 | 5fluorouracil | 250 mg |
| 05/10 | 5fluorouracil | 250 mg |
| 05/10 | Oncostatin IV | 3 mg |

-continued

| DATE | DRUG | DOSE |
|---|---|---|
| | Hyaluronic Acid III | 10 mg |
| 05/11 | carboplatin | 250 mg |
| 05/11 | vinblastine | 5 mg |
| 05/11 | mitomycin | 4 mg |
| 05/11 | calcium leukovorin | 40 mg |
| 05/11 | 5fluorouracil | 250 mg |
| 05/11 | 5fluorouracil | 250 mg |
| 05/12 | carboplatin | 100 mg |
| 05/12 | vinblastine | 2 mg |
| 05/12 | 5fluorouracil | 250 mg |
| 05/12 | 5fluorouracil | 250 mg |
| 05/12 | calcium leukovorin | 40 mg |
| 05/12 | Oncostatin IV | 2 mg |
| | Hyaluronic Acid | 20 mg |
| 06/19 | mitomycin | 5 mg |
| | Hyaluronic Acid | 10 mg |
| 06/19 | vinblastine | 5 mg |
| | Hyaluronic Acid IV | 10 mg |
| 06/19 | 5fluorouracil | 250 mg |
| | Hyaluronic Acid IV | 10 mg |
| 06/19 | 5fluorouracil | 250 mg |
| | Hyaluronic Acid IV | 10 mg |
| 06/19 | calcium leukovorin | 40 mg |
| 06/19 | Oncostatin IV | 3 mg |
| | Hyaluronic Acid | 50 mg |
| 06/20 | 5fluorouracil | 250 mg |
| | Hyaluronic Acid IV | 10 mg |
| 06/20 | 5fluorouracil | 250 mg |
| | Hyaluronic Acid IV | 10 mg |
| 06/20 | calcium leukovorin | 40 mg |
| 06/20 | mitomycin | 5 mg |
| | Hyaluronic Acid IV | 10 mg |
| 06/20 | vinblastine | 5 mg |
| | Hyaluronic Acid IV | 10 mg |
| 06/20 | Oncostatin IV | 3 m |
| | Hyaluronic Acid IV | 50 mg |
| 06/21 | Carboplatin | 20 mg |
| | Hyaluronic Acid IT | 10 mg |
| 06/21 | methotrexate | 12.5 mg |
| 06/21 | carboplatin | 150 mg |
| | Hyaluronic Acid IV | 50 mg |
| | Oncostatin IV | 3 mg |
| | Hyaluronic Acid IV | 50 mg |
| 06/22 | carboplatin | 100 mg |
| | Hyaluronic Acid IV | 10 mg |
| 06/22 | Oncostatin IV | 3 g |
| | Hyaluronic Acid IV | 50 mg |
| 06/23 | Oncostatin IV | 3 g |
| | Hyaluronic Acid IV | 50 mg |
| 08/16 | calcium leukovorin | 40 mg |
| 08/16 | 5fluorouracil | 500 mg |
| | Hyaluronic Acid IV | 50 mg |
| 08/16 | carboplatin | 250 mg |
| | Hyaluronic Acid IV | 100 mg |
| | Oncostatin IV | 3 g |
| | Hyaluronic Acid IV | 100 mg |
| 08/17 | carboplatin | 200 mg |
| | Hyaluronic Acid IV | 150 mg |
| 08/17 | carboplatin | 30 mg |
| | Hyaluronic Acid IV | 50 mg |
| 08/17 | adriamycin | 2.5 mg |
| | Hyaluronic Acid | 10 mg |
| | Oncostatin | 3 g |
| | Hyaluronic Acid | 100 mg |
| 08/18 | 5fluorouracil | 500 mg |
| | Hyaluronic Acid | 100 mg |
| 08/18 | calcium leukovorin | 40 mg |
| | Oncostatin IV | 2 g |
| | Hyaluronic Acid | 200 mg |

He was also treated with phloretin in hyaluronic acid. His tumor was injected with the following chemotherapeutic agents in hyaluronic acid:

| DATE | DRUG | DOSE |
|---|---|---|
| 05/11 | methotrexate | 12.5 mg |
| | hyaluronic acid | 50 mg |
| | adriamycin | 1 mg |
| 06/21 | methotrexate | 12.5 mg |
| | carboplatin | 20 mg |
| | hyaluronic acid | 10 mg |
| 08/18 | carboplatin | 30 mg |
| | hyaluronic acid | 50 mg |
| 08/18 | adriamycin | 25.5 mg |
| | hyaluronic acid | 10 mg |

He has had regression of his disease by 50 per cent in a situation that is otherwise not treatable. This therefore documents that unresponsive tumors can respond to chemotherapy when administered in hyaluronic acid and/or salts thereof.

CASE VII:

Female patient, aged 58, had a massive cancer of the breast with supraclavicular and auxiliary lymph nodes palpable. This has been confirmed by a biopsy. She was treated with combination systemic therapy and hyperthermia and did not improve significantly. She then received radiation from December, 1988 to January, 1989. She was subsequently seen again by Dr. Falk on May 17, 1989 and had not had a response to therapy to date. She then developed a plural effusion. She was treated by Dr. Falk by a combination of chemotherapeutic agents as follows:

(Hyaluronic Acid may be Sodium Hyaluronate)

| DATE | DRUG | DOSE |
|---|---|---|
| 05/16 | methotrexate | 25 mg |
| | Hyaluronic Acid IT | 10 mg |
| 05/16 | methotrexate | 25 mg |
| | Hyaluronic Acid axilla IT | 10 mg |
| 05/16 | methotrexate | 25 mg |
| | Hyaluronic Acid SC node IT | 10 mg |
| 05/16 | Oncostatin IV | 3 g |
| | Hyaluronic Acid | 20 mg |
| 05/17 | 5fluorouracil | 250 mg |
| 05/17 | 5fluorouracil | 250 mg |
| 05/17 | vinblastine | 5 mg |
| 05/17 | mitomycin | 5 mg |
| 05/17 | Oncostatin IV | 3 mg |
| | Hyaluronic Acid | 30 mg |
| 06/02 | methotrexate | 25 mg |
| | Hyaluronic Acid IT | 30 mg |
| 06/02 | vinblastine | 5 mg |
| | Hyaluronic Acid IV | 10 mg |
| 06/02 | Oncostatin IV | 3 g |
| | Hyaluronic Acid | 30 mg |
| 06/05 | 5fluorouracil | 250 mg |
| | Hyaluronic Acid IV | 10 mg |
| 06/05 | 5fluorouracil | 250 mg |
| | Hyaluronic Acid IV | 10 mg |
| 06/05 | calcium leukovorin | 35 mg |
| 06/05 | vinblastine | 5 mg |
| | Hyaluronic Acid IV | 10 mg |
| 06/05 | Oncostatin IV | 3 g |
| | Hyaluronic Acid | 30 mg |
| 06/21 | carboplatin | 20 mg |
| | Hyaluronic Acid IT | 10 mg |
| 06/21 | methotrexate | 12.5 mg |
| 06/21 | vinblastine | 5 mg |
| | Hyaluronic Acid IV | 10 mg |
| 06/21 | mitomycin | 5 mg |
| | Hyaluronic Acid IV | 10 mg |
| 06/21 | Oncostatin IV | 3 mg |

| DATE  | DRUG               | DOSE     |
|-------|--------------------|----------|
|       | Hyaluronic Acid    | 50 mg    |
| 07/10 | carboplatin        | 12.5 mg  |
|       | Hyaluronic Acid IT | 20 mg    |
| 07/10 | methotrexate       | 12.5 mg  |
|       | Hyaluronic Acid IT | 20 mg    |
| 07/10 | Oncostatin IV      | 3 g      |
|       | Hyaluronic Acid    | 50 mg    |
| 07/12 | Oncostatin IV      | 2 g      |
|       | Hyaluronic Acid    | 50 mg    |
| 08/14 | vinblastine        | 5 mg     |
|       | Hyaluronic Acid IV | 50 mg    |
| 08/14 | 5fluorouracil      | 50 mg    |
|       | Hyaluronic Acid IV | 50 mg    |
| 08/14 | calcium leukovorin | 30 mg    |
| 08/14 | Oncostatin IV      | 3 g      |
|       | Hyaluronic Acid    | 100 mg   |
| 08/16 | Oncostatin IV      | 3 g      |
|       | Hyaluronic Acid    | 100 mg   |

She had also had a thoracentesis with subsequent instillation of 5fluorouracil, mitomycin C and hyaluronic acid into the chest cavity. Her pleural effusion is totally resolved. The lesions in her breast continue to recede and her supraclavicular and axillary lymph adenopathy is totally gone.

This patient represents a response with relatively low doses of hyaluronic acid and/or salts thereof added to conventional chemotherapy used systemically by injection into the tumor and by intra-pleural cavity instillation. The response has been further enhanced by the use of phloretin in synacid T.M. (hyaluronic acid and/or salts thereof) at the same time.

Follow-Up

At a much later date this patient is in remission and doing very well.

CASE VIII:

This is a 62 year old female treated previously with systemic chemotherapy, two different drug combinations without any response. She was referred for treatment including hyperthermia, and direct chemotherapy injections to which she responded initially, beginning September.

She was noted in April-May, to have an increase in the tumour in the right upper lobe of her lung. This tumour was an anaplastic small cell carcinoma. The tumour was treated by injecting into the lesion bleomycin with hyaluronic acid and indomethacin with hyaluronic acid. She also received systemically indomethacin 300 mg daily with 300 mg hyaluronic acid. The patient was followed radiologically and improved very dramatically over the next 2 to 4 weeks. The last film report shows that the left hemi-thorax is clear. On the right side there is no evidence of pleural reaction. There is a prominent right upper lobe volume loss with elevation of the right hilum. The area of increased lucency in the right apex may represent a region of cavitation within the collapsed lobe or elevation of the superior segment of the right lower lobe. Comparison with previous films shows that the mass has decreased significantly in size and cannot now be distinctly identified on this examination.

The applicants believe that this response is a direct result of the carrier molecule—hyaluronic acid—injected with a chemotherapeutic agent and with a non-steriodal anti-inflammatory drug to assist in clearance of the necrotic tumour.

CASE IX:

This patient was diagnosed as having a gastric cancer July, 1988 and it was deemed unresectable. A gastroenterostomy-type of bypass was performed. Saw the patient initially in August and treatment was initiated in September, 1988. At that time he was heated and received phloretin with very low dose chemotherapy employing 5-FU plus immune augmenting agents.

This therapy essentially was continued until February, 1989 when Dr. Falk began to use DMSO as a carrier/penetrating agent in addition to MSN. He did receive increasing amounts of chemotherapy employing 5FU leukovorin, mitomycin C and methotrexate and subsequently in July and early August, as there was tumor progression, he also received novantrone.

As of May he began to receive these drugs in hyaluronic acid but the initial amounts of hyaluronic acid were small, employing 10–30 mg per average dose with the original drug i.e. phloretin, or the chemotherapeutic agent. There was some initial improvement in his status but then in mid August he progressed to a situation where there was increasing evidence of gastric obstruction, and also obstruction of the biliary tree with jaundice and elevation of the bilirubin. Dr. Falk then treated with higher doses of hyaluronic acid to a total dose of 500–600 mg of hyaluronic acid divided among the different drugs. The patient continued to receive the same types of drugs.

While his condition initially deteriorated, an upper gastrointestinal series performed on September the 7th shows his gastric bypass to be totally open whereas prior to this the patient had been vomiting all oral intake. His status has now steadily improved.

On the basis that the patient received identical drugs earlier, the improvement must be attributed to the higher doses of the carrier molecule, allowing for better penetration of drug into what is always a scarred, fibrotic tumor and generally fatal at this stage.

Follow-Up

Unfortunately at a subsequent date, patient died as a consequence of tumor necrosis and scar tissue developing—not from cancer.

CASE X:

Patient was diagnosed as having a hepatoma now over 2 years age. The tumor had been stable or with minimal growth over the past 18 months. Since treatment with low dose chemotherapy and the carrier/penetrating molecule, hyaluronic acid, she appears to have had a complete response. Her alkaline phosphatase is now at 150 international units and the remainder of her liver function tests are essentially normal. Her ultrasound show no distinct tumors anymore in the liver. Dr. Falk is now treating her once every 2–3 months.

Follow-Up

This patient is still doing well.

CASE XI:

This patient was infused on Jun. 15, 1989 with chemotherapy with added hyaluronic acid on one occasion. She then received hyperthermia. Previously with multiple hepatic metastases from cancer of the breast she had been stable on tamoxifen, the estrogen-blocking substance.

After one course of infusion of only 8 hours she has had what would appear to be a complete response. Her ultrasound now shows no tumor present in the liver and her liver function tests are all normal.

For the present no further treatment necessary are following her and continuing her on tamoxifen to block the estrogen receptor.

Follow-Up

This patient relapsed after another doctor gave vaginal estrogen cream (tamoxifen) to her for vaginal irritation. In response, patient was given treatments of 300 mg of indomethacin in 300 mg of hyaluronic acid daily. She is now in remission.

CASE XIA:

This patient had a massive leomyosarcoma of the uterus resected on Mar. 26, 1989. There was residual tumor present as demonstrated by a CAT scan. Dr. Falk has treated her with a combination of hyperthermia, very low dose methotrexate using this intraperitonealy with a carrier/penetrating molecule—hyaluronic acid and then using the agent that blocks glucose transport protein—phloretin, also with hyaluronic acid and alpha II interferon intraperitonealy again combined with hyaluronic acid.

On sequential CT scan this patient shows significant improvement in size of the residual mass. As soft tissue sarcomas are so very resistant to all forms of therapy this could be described as an unusual response and is in all likelihood related to the use of the carrier/penetrating molecule—hyaluronic acid. Dr. Falk is now treating this patient approximately every 6–8 weeks for 2 days and hopefully her regression of tumor will continue. If that is the case, than one could consider closing her colostomy in about 6 month's time.

Follow-Up

Some tumor grew back. Patient was given treatments of Vitamin C (50 mg daily), indomethacin (300 mg daily) in 300 mg of hyaluronic acid. This patient is feeling much better.

CASE XIB:

This patient has received relatively low doses initially of methyl CCNU and carboplatin with methotrexate injected into the inguinal recurrent melanoma. All of these molecules were given in the carrier/penetrating agent hyaluronic acid. In addition she received the agent that blocks glucose transport which Dr. Falk has developed. This is a molecule called phloretin which was used many years ago. It has been solubilized in a special solution and is also given with hyaluronic acid as it will also enhance the penetration of this molecule into the tumor. Dr. Falk then treated her with hyperthermia using both capacitive and inductive radio frequency hyperthermia and microwave hyperthermia. In addition she has received immune stimulating agents which Dr. Falk believes will produce benefit but only in conjunction with other agents.

In the last 2 courses of treatment she has received only carboplatin with added hyaluronic acid, phloretin with added hyaluronic acid and methotrexate administered now by intra-peritoneal route at a low dose—25–35 mg in hyaluronic: acid again.

Dr. Falk saw her this week and he will treat her for 2 days. She is clinically in excellent condition. She has the one complaint of right-sided back pain. On examination one does have the impression that this could be tenderness over the right kidney. The ultrasounds of her kidneys have suggested a solid mass in the right kidney which was interpreted as being either a hamartoma or even an angiomyolipoma.

In view of the patient's rather dramatic response Dr. Falk thinks it would be worth while to get a CAT scan done of the abdomen. There is still the question of a small cystic lesion in the right lobe of the liver but her liver function in now normal.

Follow-up

This patient is now in complete remission.

CASE XII:

The patient had an arterial line and subcutaneous port installed at the time of the original abdominal surgery. He came to see Dr. Falk and it was noted that there was redness, in duration and swelling around the subcutaneous port. The patient had a febrile response and elevation of his leukocytes.

A £ 14 gauge plastic cannula was inserted into the area and 75 cc of purulent material was drained and cultured growing *E. coli* and *Pseudomonas aeruginosa.* Dr. Falk treated him by irrigating the site with a combination of hyaluronic acid with ampicillin, hyaluronic acid with flagyl., and hyaluronic acid with keflosporin. Thus the wound was irrigated on a daily basis with 1 gram of ampicillin with 50 mgs. of hyaluronic acid, 500 mgs. flagyl with 50 mgs. of hyaluronic acid and 1 gram of Ancef with hyaluronic acid. During the first 2–3 days irrigation it was possible to continue to aspirate purulent material from the subcutaneous site. Within 5 days there was no purulent material remaining and there was just fluid present and by the end of the week there was no residual infection present. The port-a-cath continued to function over the next three months of the patient life.

This is cited as an example of anti-bacterial agents with added hyaluronic acid producing better penetration of the various different anti-bacterial drugs into the site of infection and one would have to postulate that there was improved penetration into the bacteria themselves.

CASE XIII:

This patient was operated on Jun. 1st, 1989 and a resection was performed of a portion rectum and sigmoid colon, and the small intestine. Post-operatively on day 7 he was noted to have swelling and induration in the wound tissue and two sites of purulent material were drained. He was treated subsequently with local irrigation with ampicillin 1 gram combined with 50 mgs. hyaluronic acid and 500 mgs. of flagyl combined with hyaluronic acid. These two areas of infection cleared of any bacterial contamination within 4 days. The usual time required would be in the order of a number of weeks.

CASE XIV:

This patient with cancer of the breast has an infected Hickman Line. This is an indwelling plastic catheter in the subclavian vein. This infection was present subcutaneously with purulent material coming from the site of the entry of the plastic cannula. In this situation Dr. Falk injected ampicillin 1 gram and 50 mgs. of hyaluronic acid directly adjacent to the plastic catheter. In addition the patient received flagyl intravenously with added hyaluronic acid. The infection cleared and the catheter was presented in a matter of 4 days.

CASE XV:

This man developed an abscess on the right upper quadrant of his abdomen, in the anterior abdominal wall. This was drained in hospital but continued to be a problem. Dr, Falk has now discharged him and begun to irrigate this with ampicillin 500 mg daily and 200 mg of hyaluronic acid. While this abscess was drained and therefore should have recovered eventually, it had taken a longer period of time than one would have anticipated. The abscess grew both *staphlyococcus aureus* and *e. coli.*

After 2 days of irrigation with ampicillin and hyaluronic acid as described, the cavity was clean, free of infection and beginning to granulate over nicely. Dr. Falk continued to treat him during the week and it healed satisfactorily.

In other patients alpha 2-interferon was combined with hyaluronic acid and applied to a patients canker sores and the sores rapidly cleared up.

In another patient, methotrexate was carried in hyaluronic acid and applied topically to a patient with psoriasis. The formulation was absorbed and the psoriasis cleared.

In ten other patients suffering from herpes simplex type I and II, the application of an effective amount of nonoxynol-9 [nonylphenoxy polyethoxy ethanol] (Delfen™) combined with hyaluronic acid and/or salts thereof to the effected areas 2 to 3 times daily gave immediate relief of the symptoms (pain) and disappearance of the lesions.

In at least two patients, an effective amount of nonoxynol-9 for treating herpes zoster (shingles) was combined with hyaluronic acid and/or salts thereof and was successfully employed to treat the herpes zoster (shingles).

CASE XVI:

A dentist with melanoma, age 51, developed acute herpes zoster in the 9th thorasic dermital on the left side of his body. He was in excruciating pain, not relieved by classical medications. Dr. Falk asked him to take orally cyclofur as an antiviral but he did not begin this immediately. However, Dr. Falk also indicated that he should take "Delfen™" and "LifeCore™" hyaluronic acid, mix equal portions and then apply this topically. He did this and had immediate relief of pain within 5 minutes. The pain has remained absent for the next 4 days. In addition, the lesions of herpes zoster immediately began to disappear within the first 24 hours and now, 5 days later, none are apparent. This is a dramatic response suggesting a major antiviral affect of this combination, with the hyaluronic acid obviously enhancing penetration.

CASE XVII:

This man developed stomach cancer which metastasized to his liver. He was treated for seven: months with low dose chemotherapy (5 FU), low doses of mitomycin and novantrone with various amounts of hyaluronic acid, and Vitamin C (50 gm daily). There was no detectable tumor. He is now in remission and all tumors are calcified.

CASE XVIII:

This male patient had a serious car accident, shortly thereafter he developed colon cancer which was resected with multiple liver metastases. He came to Dr. Falk in June, 1989. He was treated with chemotherapy (phloretin) and hyaluronic acid with heat. He remained stable for approximately one year, then his alkaline phosphatase began "creeping up". Consequently, Dr. Falk treated him with Vitamin C (50 gm daily for three days), hyaluronic acid (up to 300 mg daily), indomethacin in N-methyl glucamine (300 mg daily in the 300 mg of hyaluronic acid), and Toradol™ (60 mg) once or twice daily with hyaluronic acid (50 mg). Since that time he has shown improvement. His alkaline phosphatase decreased, and therefore his liver is functioning better.

CASE XIX:

This man, age 46, was diagnosed in the last three months with a difficult to treat broncheolar alveolar carcinoma of the lung. Appropriately, neither chemotherapy nor major amounts of radiation were used, although spot radiation was given to two areas; one on either side of the chest where there apparently was some indication of skeletal involvement.

Subsequent to that, the patient visited a cardiopulmonary transplant unit in London who thought that a transplant might be appropriate but there was a waiting list of about one year.

After this the patient went to Dr. Frederick Douwe's clinic in Germany and was placed on a variety of regimens, the main direction of which includes; (a) immune enhancement at the T-cell level; and (b) free radical scavenging and detoxification.

He has improved somewhat since this treatment was initiated with episodes when he is very short of breath, having had one of those 24 hours ago.

On examination he has very severely diminished air entry on both sides with bilateral rales and ronchi. There is no evidence of supraclavicular adenopathy. There is not evidence of skeletal tenderness at this point or of hepatic enlargement.

He then came to Dr. Falk and he treated him with Vitamin C (50 gms), non-steroidal indomethacin (NSAID)(100 mg —reduced from initial amount of 300 mg because of heartburn) dissolved in hyaluronic acid (300 mg). He improved dramatically after the first 5 days of therapy with reference to lung capacity and radialogical appearance on the X-ray.

Dr. Falk then prescribed daily injections of hyaluronic acid (300 mg) with Toradol™ (60 mg) to be taken at home ("home" being outside of Canada).

Comparison has been made to the previous examination. Since that previous examination, there has been resolution of some of the increased interstitial markings so that the lungs now look clearer than they did on the previous exam. Nonetheless, increased interstitial markings are still present within both lung fields.

CASE XX:

A female patient, age 74, was diagnosed with cancer of the colon and was resected. The cancer had however mestastasized to the liver (right lobe). Over a one month period, she was treated twice with methotrexate (25 mg) in hyaluronic acid (400 mg) intraperitoneally, five times with oncostatin (2 gm) in hyaluronic acid (300–500 mg), Vitamin C (50 gm) in hyaluronic acid (300 mg), and indomethacin (NSAID) given twice, 100 mg of indomethacin in 300 mg hyaluronic acid and 250 mg of indomethacin in 500 mg of hyaluronic acid.

The patient is now doing very well, feeling better, and the liver tumor is regressing (shrinking).

CASE XXI:

This female patient, age 51, was diagnosed with cancer of the uterus which had spread to the lungs (leiomyosarcoma). Dr. Falk treated her with various doses of oncostatin (low doses of 0.5 gm to 3 gm) with hyaluronic acid (300–500 mg), Vitamin C (50 gm) in hyaluronic acid (300 mg), and indomethacin in hyaluronic acid (intraperitoneally and intravenously).

The pelvic mass is presently regressing and the lungs are now stable.

CASE XXII:

This man, age 52, has a history of Crohn's Disease and chronic infection in the bowel from Crone's disease. He eventually developed a tumor in the peritoneum (adenocarcinoma). The patient was treated with doses of 2 gm and 3 gm of Oncostatin™ (phloretin) each in hyaluronic acid (500 mg) and DMSO (total of 2000). Doses of indomethacin ranging from 75 mg to 450 mg in 200 to 700 mg of hyaluronic acid were given. Patient was also treated with Vitamin C (50 gm) in hyaluronic acid (300 mg), and naproxen (1 gm) in hyaluronic acid (400 mg). These treatments were given to the patient via several routes intraperitoneally, intravenously, rectally (for detoxification) (insertion of catheter and administered rectally). The pain is now gone.

Patient was given CT Scan of the abdomen and pelvis. There is moderate hepatic steatosis without evidence of metastatic disease. The spleen, pancreas, adrenals and right kidney appear normal. There is a left nephrostomy tube in place with no evidence of residual hydronephrosis. There is a large and necrotic tumor mass occupying most of the deep pelvis with anterior displacement of the urinary bladder and likely some invasion of the prostate gland. There is no evidence of sacral destruction although the rectal tumor is closely apposed to its anterior surface.

Thus there appears to be a large and necrotic pelvic tumor mass without evidence of sacral destruction, para-aortic lymphadenopathy or distal visceral metastases. A left percutaneous transrenal ureteral stent is in place.

The patient was seen Aug. 1, 1990, in the clinic and he has been feeling very well. He is doing extremely well; the necrotic tumor mass is slowly reducing in size.

CASE XXIII:

This female patient, age 47, was diagnosed in January, 1990. A gastric resection and colonic replacement of oesophagus (for swallowing) was performed. She had also developed an intraperitoneal tumor. She was given chemotherapy and lost her hair. (Dr. Falk gave her minoxidil and hyaluronic acid to apply to her scalp and her hair grew back). Dr. Falk saw this patient on Jun. 6, 1990, and gave her lower doses of phloretin together with heat and hyaluronic acid, indomethacin in hyaluronic acid, and Vitamin C in hyaluronic acid.

Since the time of treatment, the patient has made good improvement. She has gained weight, and is no longer feeling any pain. The carcinoembryonic antigen is down to 26 nonograms/ml and steadily falling.

CASE XXIV:

This man (age 45). first seen by Dr. Falk on Mar. 1, 1988, he was diagnosed with carcinoma of the pancreas. He was treated with DMSO and heat together with low doses of chemotherapy. Dr. Falk injected the DMSO and the other drugs into the tumor. More than one year later, this patient was given treatments with Vitamin C, and other agents in hyaluronic acid. This patient is now in complete remission. He has not been treated in more than six months.

CASE XXV:

Dr. Falk saw this female patient (age 62) in August, 1989. This woman was diagnosed with carcinoma of the pancreas. She was treated with low doses of chemotherapy (5-FU and mitomycin) together with 300 mg of hyaluronic acid and heat. She was having trouble with her bile ducts. She was operated on, but a tumor was not found and the bile ducts were bypassed. The patient was then treated with indomethacin and Vitamin C in hyaluronic acid, and the heating treatments were stopped. Since her treatment she has experienced a gain in weight and there is no evidence of a significant tumor.

CASE XXVI:

This female (age 18) patient was treated for infectious mononucleosis. Three months of testing the patient resulted in positive heterophile antibody tests. Patient had no energy. The patient was given 50 gm of Vitamin C and 300 mg of hyaluronic acid. Within sixteen hours of the treatment her energy increased dramatically and within two weeks the heterophile antibody test became negative.

CASE XXVII:

This woman (age 65) patient illustrates important points. Her previous chemotherapists did not recognize they had killed most of her tumor. She had been taking chemotherapy previously. However as the tumor was breaking up, as Dr. Falk has now concluded, there was a retention of water fluid in the area of the tumor (they should have looked at the ultrasound for assistance). Dr. Falk saw her and treated her with heat, phloretin, Vitamin C, indomethacin and some 5-FU, all in hyaluronic acid. (According to her previous doctors, she had an enlarged tumor after taking 5-FU. Therefore, they stopped chemotherapy). The patient is now looking better and feeling better and there is no edema.

CASE XXVIII:

This female patient had carcinoma of the ovary with intermittent to complete bowel obstruction with encasement of the bowel with tumor and also significant amounts of pleural fluid. The most striking example of the effect of Lasix (furosemide) occurred under the following circumstances. On Apr. 28th and 29th, 1990, the patient excreted a total volume of 2,450 ml of urine over 48 hours despite the administration of 0.33 per cent sodium chloride solution with added potassium chloride at 40 mEq/l administered at the rate of 100–125 ml per hour. The patient's body weight was 40 kg. During this period of time the patient received 120–200 mg of Lasix administered intravenously.

On April 30th, she received 40 mg of Lasix with added 350 mg of hyaluronic acid administered over half of an hour. She produced a diuresis within the following 5 hours of 2,500 ml of urine. During the evening hours with no additional Lasix being given, urine output fell dramatically and she excreted only 400 ml of urine from 7:00 p.m. April 30th to 7:00 a.m. May 1st. At 7:30 a.m. she received 40 mg of Lasix in 300 mg of hyaluronic acid administered intravenously. Over the next 8 hours, this patient produced 2,600 ml of urine. This case demonstrates the fact that even a relative insensitivity to furosemide (Lasix) can be overcome with the addition of hyaluronic acid to enhance drug penetration to the appropriate area.

The similar type of phenomena has been observed by us in patients where there is a so called "hepatorenal syndrome" and where the kidney stops excreting urine due to the failure of the liver to function adequately. Under these circumstances, urine output may decrease to essentially zero levels. This can be dramatically effected by furosemide (Lasix™) administered intravenously in hyaluronic acid, even though furosemide (Lasix™) administered by itself produced no effect.

CASE XXIX:

In normal healthy individuals, it was observed that adding hyaluronic acid to furosemide (Lasix™) administered at a dose of 20 mg intravenously with 300 mg of hyaluronic acid, there was an increase of urine excretion by 3 to 5 fold as compared to that observed with furosemide (Lasix™) alone. This is cited as evidence that hyaluronic acid increases penetration/permeation of the drug and thus facilitates its function.

CASE XXX:

This balding patient applied minoxidil (Rogaine) topically to his scalp. There was minimal or little hair growth. Subsequently, the minoxidil was applied together with hyaluronic acid continuously every 2 to 3 days. As a result this patient's hair has grown fuller and more rapidly.

CASE XXXI:

This female patient (age 32) was diagnosed as having an epitheloid sarcoma on the basis of a Mayo Clinic review.

Her history of the disease dates back to Dec. 12, 1978, when she developed nodularity in the left ring finger which was excised. She has had recurrent episodes of this type of problem since then and has had an amputation of the left 4th finger. She has been extensively staged and investigated as she was found to have nodules of the same type of disease up her arm and a left axillary lymph node biopsy was positive in March, 1990 for an epitheloid sarcoma.

At the Mayo Clinic she received three courses of chemotherapy with mitomycin C, adriamycin, cisplatinum in high doses without any response. She was scheduled for a forequarter amputation for the sarcoma of the left arm and forearm.

This patient was first seen by Dr. Falk on Jun. 25, 1990, and was treated for three days with heat, phloretin-hyaluronic acid, vitamin C-hyaluronic acid, methotrexate-hyaluronic acid, and also received solu-medrol. She did not have a clear response at that point in time and the lesions remained the same.

She returned on July 23 and was treated for three consecutive days with a reduced dose of phloretin, same dose of vitamin C-hyaluronic acid and received both naproxen and indomethacin with hyaluronic acid both subcutaneously and intravenously. She returned home and received Toredol™ (Syntex—non-steroidal anti-inflammatory drug) intramuscularly on a daily basis at a dose of 30–120 mg administered once or twice per day with 100 mg of Hyal Pharmaceutical type hyaluronic acid.

She was reassessed on August 20 and has had a dramatic decrease in size of all measurable disease by greater than 50%. In fact, at this point, biopsy would have to be done to ascertain if there is any viable tumor present. The treatment plan is to continue on the Toredol™ and hyaluronic acid.

While the patient had some minimum response with heat, phloretin, conventional chemotherapy with the addition of hyaluronic acid with these drugs, she did have an excellent response with the non-steroidal anti-inflammatory drugs using all three types; Indocid™, naproxen and Toredol™ when combined with hyaluronic acid as a carrier/penetrating vehicle to facilitate targeting to pathological tissue. She has had few if any of the standard side-effects that occur with the non-steroidal anti-inflammatory drugs.

CASE XXXII:

This male was diagnosed as having gastric cancer in 1988. The tumor was in the distal third of the oesophagus at the gastro-oesopageal junction. A Celestine tube was placed by an intraoperative abdominal procedure and sutured to the lesser curvature of the stomach.

The patient was treated from January, 1990 up until 3 months ago (June, 1990). Repeated CAT scans have shown no change in any situation; symptomatically he had been completely well. Most recent CAT scan was Jun. 26, 1990. This raised questions in respect of some areas in the liver; however, sonographic examination suggested that these were in fact homogenous.

On July 4th he had some "hot dogs" at a picnic. During the night he woke up with acute left upper quadrant pain which was not associated with nausea or vomiting. Subsequent to this he had episodes of pain essentially every time he consumed any food. The pain was always the same, felt in the back and the front of the abdomen and tended to "spread" to both flanks. It has never been associated with any direct peritoneal tenderness, vomiting, diarrhea or fever and chills. Investigation included the previous CAT scan done just eight days prior to the onset of this pain, and an upper GI series with follow-through. Further CAT scan now could not be done because he was still full of barium.

It is important to recognize that a significant dose of Demerol just barely relieved his pain. Further examination is unremarkable. There were no abdominal, thoracic or lymph node findings to suggest any spread of the disease.

Dr. Falk reviewed the X-rays with a Professor at the Department of Radiology, Toronto General Hospital, University of Toronto. He suggested that the upper GI series was a classical picture of "tethering" of the small bowel. He said, this could be either from fibrous adhesions or from neoplastic disease, or indeed, a combination of both, as is very common with adenocarcinoma of the stomach. However, the neoplastic seedings would necessarily be very minimal, as nothing shows on the previous CAT scan.

Dr. Falk treated the patient with a combination of non-steroidal anti-inflammatories administered intravenously with hyaluronic acid in conjunction with hyperthermia and oncostatin, which is a combination of phloretin and hyaluronic acid and achieved almost immediate relief of pain. He can now eat without having symptoms (had lobster soup recently at one of the local restaurants).

Dr. Falk has also given him a supply of probanthine which he could use, as the type of pain that occurs with these type of adhesions is usually relieved by one of the anti-cholinergic drugs. Dr. Falk has also suggested to him to come back for further therapy and continue when he goes home on a combination of felden 10 mg b.i.d. and naprosyn 500 mg directly as suppository once per day and take zantac 150 mg twice a day.

In addition Dr. Falk placed him on Vibramycin (Doxycyline) 200 mg for one day and a 100 mg daily dosage for fourteen days. This is an antibacterial agent and also blocks intracellular and anerobic glycolosis.

Follow-Up

Recent biopsies showed chronic inflammation of the lower one third of the oesophagus (tube in oesophagus recently removed); however, there were no malignancies found.

CASE XXXIII:

This man has had major tumor breakdown and this has occurred only after chemotherapy was omitted from the treatment regimen. This initially made him significantly more ill; this was reflected only to a minor extent in terms of his hepatic function tests. The alkaline phosphatase did become elevated. He had profound malaise, weakness, excessive fatigue and loss of appetite. This has been corrected by intensive use of indomethacin in hyaluronic acid and detoxification programs.

He was reassessed and was significantly better. Under ultrasound, the tumor shows virtually total necrosis. There is now increased normal liver tissue present.

CASE XXXIV:

This man had a chronic abscess cavity in his pelvis with a bowel obstruction which necessitated an operation on Jan. 5, 1990. At that time the cavity was irrigated out and drained through the perineum. He had an uneventful post-operative course and was discharged from hospital on Jan. 18, 1990.

However, subsequently he developed a fever and because this had been a large cavity in the pelvis, it now drained through the lower anterior part of his abdominal incision. This occurred two weeks prior to the present visit.

Dr. Falk assessed him. This is a large cavity and he thought that this would take 4 to 6 weeks to close. Dr. Falk instituted daily irrigations during the 5 day working week with ampicillin, flagyl and hyaluronic acid using 500 mg of ampicillin and 500 mg of flagyl. This is a very benign form of treatment in contrast to what Dr. Falk would usually use which would consist of irrigation and packing the area open.

When seen later, the abscess cavity had closed over. The patient advised that the visiting nurse on the weekends had difficulty putting a catheter into this cavity over Saturday and Sunday and in fact could not gain entrance of the catheter. Dr. Falk concluded that the cavity had granulated in from the "bottom up" but has done so much more rapidly than he would have anticipated. In view of the fact that this is a chronic cavity in a patient who has had a chronic and ongoing problem in the pelvis, this is clearly an unanticipated result with a much more rapid and better resolution of a chronic abscess cavity than anticipated.

Dr. Falk has instructed the patient to call if he develops any temperature subsequent to this. He has had a mild itching sensation over his skin which Dr. Falk believes is probably a reaction to cold and for which he gave him an ointment to be applied daily.

CASE XXXV:

Woman had a 9th and 12th nerve lesion, which was thought was located just lateral to the base of the skull. It was also thought that she may have had metastases in the region of the dentoid process, and an MRI scan was undertaken to try and demonstrate this. It showed somewhat abnormalities in the appropriate area. A CT scan of the region was unhelpful.

The patient then attended The Ontario Cancer Treatment and Research Foundation and was found to have very advanced malignant melanoma, and was discharged from the hospital with a hopeless prognosis.

Much later the people of Ontario Cancer Treatment and Research Foundation were surprised and delighted to find that she had responded unbelievably well to both positive mental imaging and to Dr. Falk's treatment. This involved hyperthermia and chemotherapy in hyaluronic acid. Dr. Falk used usual doses of Carboplastin and low doses of Methotrexate in the hyaluronic acid.

Her chest now appears clear, and she has some persistent lesions in kidney and liver, but these may well be under control. During the summer, her tongue got better, and no longer deviated to the left. However, during the last three or four weeks, things have deteriorated from that point of view.

On recent examination, the neurological examination was entirely normal, except for a deficit (incomplete) ingag on the left side of the pharynx, and a problem with some fasciculations and atrophy of the left side of her tongue.

This patient has done remarkably well.

Follow-up

More recently this woman has been administered hyaluronic acid (300 mg daily), NSAID and Vitamin C (50 gm daily). The patient appears now to be clear of tumour.

CASE XXXVI:

This man has a mesothelioma following surgical resection and then adjuvant treatment. It is now seven years since the initial diagnosis. In the spring of this year he developed a recurrence while in Florida. Although Dr. Falk has biopsied this three times, Dr. Falk has never obtained cells diagnostic of malignancy. However, clinically the situation is very clear from the CAT scan, liver function test and ultrasound.

This patient has been treated with phloretin in hyaluronic acid, and heat to the area. Initially, he did not show a major response. However, on the last occasion he received no chemotherapy and only phloretin in hyaluronic acid with a higher dose of hyaluronic acid. He has had a major response and has had major problems with accumulation of fluid, Dr. Falk believes, secondary to tumor breakdown. The tumor breakdown is clearly apparent on the sonographic assessment; here there is actual liquification of the tumor.

During his present stay, he was treated one day with hyperthermia and received phloridzin in hyaluronic acid. However, he required an additional two days of treatment with Vitamin C in hyaluronic acid to assist in detoxification. He also received additional diuretics Lasix™ (furosemide) with hyaluronic acid.

His creatinine which was 400m mols/l has decreased to 155y mols/l (kidney function tests-went from high to almost normal). Dr. Falk has instructed him regarding further management. Dr. Falk does not think the patient will require major further therapy as Dr. Falk thinks the majority of this tumor has been destroyed, through his own immune response, the antibody and the soluble mediators being allowed to enter into the tumor by hyaluronic acid.

In July, 1990 moderate ascites (fluid in body) occurred. The patient was given furosemide (Lasix™) and hyaluronic acid, indomethacin and hyaluronic acid. The patient's urine output increased substantially and the problem cleared.

CASE XXXVII:

A 37 year old female had a carcinoma of the cervix which was a class IIIB at the time of diagnosis. She was treated by radiation at the Cross Cancer Centre, unsuccessfully, and developed further growth of the tumor which was diagnosed approximately 1 to 2 months after the radiotherapy. She was then seen by Dr. Walde at the fault Ste. Marie hospital. He administered epirubicin, cisplatinum at high doses and did produce regression of the tumor as assessed by intravaginal assessment and biopsy, but apparently there was regrowth and worsening of the pain with partial ureteric obstruction demonstrated as shown by a CT scan of the abdomen and pelvis done Jun. 28, 1990.

At laparotomy, the patient had extensive tumor with major areas of necrosis but tumor extending to and involving the left common iliac artery and vein producing obstruction of the vein, the tumor was considered not resectable for surgical cure because of its extent in the lateral true and false pelvis to the pelvic wall. This was assessed by a urological and two general oncological surgeons.

For this reason and because of imminent rectal obstruction, a colostomy was performed. In addition, the urological surgeon established an ileal conduit.

This patient was in excruciating pain continuously for several weeks prior to and after the surgical procedure. This necessitated high doses of intravenous morphine with only partial control of the pain. On July 8th she was noted to have a major febrile reaction and a CAT scan that day showed an abscess in the left pelvis. This was drained under CAT scan localization and the patient was placed on systemic antibiotics with only slight improvement in her infectious symptoms.

She was brought to Dr. Falk on Wednesday, July 11th. She received 1 gm of ampicillin through the draining catheter for the abscess with 500 mg of hyaluronic acid. In addition, she received 1 mg of ampicillin intravenously and ancef and flagyl systemically in 500 mg "LifeCore™" hyaluronic acid. She also received 100 mg of indomethacin with 500 mg LifeCore™ hyaluronic acid intravenously. Within 12 hours her pain had dramatically decreased, all infective symptoms were eliminated and the drainage from the abscess cavity had almost stopped. Her massively enlarged left leg due to venous and lymphatic obstruction improved to almost normal size within a 12 hour period of time.

The patient was subsequently treated further with the same regimen for the next 3 days resulting in total relief of pain and continued improvement in her status, to the point where she could be discharged from the hospital on July 18th without anti-biotic therapy. Her systemic analgesia with morphine agents had been eliminated. There was no hyperthermia and no cytosis chemotherapy and/or Oncostatin (phloretin) utilized in this patient. She received antioxidant therapy with hyaluronic acid concomitantly with the indomethacin-hyaluronic acid. This patient has demonstrated a very dramatic improvement emphasizing that the indomethacin-hyaluronic acid is targeting specifically to pathological tissue improving macrophage function at this site and allowing the body's immune system to perform appropriate tumor destruction.

CASE CASE XXXVIII:

A male patient suffering from HIV (AIDS) was treated with indomethacin (NSAID), Vitamin C, interferon and DMSO and/or hyaluronic acid and unexpectedly the patient is steadily improving.

CASE XXXIX:

A male patient suffering from kyphosis suffered from constant back pain. Taking analgesics orally and rubbing back preparations onto his back, did little to alleviate the back pain. When NSAIDS in hyaluronic acid (sodium hyaluronate) were applied directly to the back, the back pain eased and disappeared.

With indomethacin (dissolved in N-methyl glucamine) and naproxen both dissolved in hyaluronic acid, the patient experienced side effects. However, with Toradol™ (the [+/−] form tromethamine salt of ketorolac—a prostaglandin biosynthesis inhibitor and analgesic and anti-inflammatory, the back pain eased and disappeared for some time and there were no side effects.

CASE XL:

This male patient was diagnosed with HIV (AIDS) and as a possible result thereof, an undetermined neoplastic disorder in the lungs. Before treatment, the patient was near death; white cell count was $1.4 \times 10^9$/liter. The patient was treated intravenously with indomethacin (300 mg), Vitamin C (50 gm daily) and hyaluronic acid (sodium hyaluronate) (300 mg). After treatment, the patient's platelet count rose to $65 \times 10^9$/liter. and his white cell count rose to $8.2 \times 10^9$/liter. His lymphocytes doubled.

Further Tests (Animal)

Further tests were conducted on animals (rats) with the indicated results:

Enhanced Activity of Antibiotics with hyaluronic acid. A chronic abscess rat model was used. Sprague Dawley Rats were used. Pellets of bacteria were inserted into each of the bellies of the rats and then the rats were treated as indicated. In this model therapeutic activity of gentamycin was compared to gentamycin in hyaluronic acid the results demonstrate a statistically significant improvement by the combination over the antibiotic alone. In this regard lower doses of antibiotic in antibiotic refractory situations were required as a result of the antibiotic being administered with hyaluronic acid. Please refer to FIG. 1/1 of the drawings.

In another animal test (Grafts from ACI strain rats (black) to Lewis Strain rats (white)), enhancement of graft survival was found by combinations of immune suppressors and hyaluronic acid (HA) administered to the Lewis Strain rats. Graft survival depends in major part on the ability to suppress graft rejection with immunosuppressive agents optimum activity of these agents is seldom achieved as they are not delivered to the graft site in effective concentrations; combinations of the agent with hyaluronic acid overcomes this difficulty. Optimization of immunosuppressive/graft survival activity by combination of specific agents with hyaluronic acid is achieved. A standard rat skin graft rejection model was used. Cyclosporin was the immunosuppressant used. The results indicate that hyaluronic acid significantly increased cyclosporin induced graft survival.

GRAFT SURVIVAL OF DIFFERENT TREATMENTS (JUL. 12, 1990)

| CYA + HA # | days | CyA # | days |
|---|---|---|---|
| 1 | 20 | 7 | 20 |
| 2 | 19 | 8 | 20 |
| 3 | 19 | 9 | 20 |
| 4 | 20 | 10 | 19 |
| 5 | 19 | 11 | 19 |
| 6 | 20 | 12 | 20 |
| 13 | 21 | 20 | 19 |
| 14 | 19 | 21 | 17 |
| 15 | 18 | 22 | 14 |
| 16 | 20 | 23 | 14 |
| 17 | 20 | 24 | 14 |
| 18 | 20 | 25 | 19 |

-continued

| CYA + HA # | days | CyA # | days |
|---|---|---|---|
| 19 | 20 | | |
| mean | 19.615 | 17.917 | |
| SE | 0.213 | 0.723 | |

CyA + HA vs. CyA = P value, one-way ANOVA = <0.05 (= 0.0287) LSDMRT = <0.05
CyA = Cyclosporin
HA = Hyaluronic Acid As many changes can be made to the invention without departing from the scope of the invention, it is intended that all material contained herein be interpreted as illustrative of the invention and not in a limiting sense.

The embodiments of the invention in which an exclusive property or privilege is claimed are as follows:

1. A method of transporting a non-steroidal anti-inflammatory drug (NSAID), and hyaluronic acid or a pharmaceutically acceptable salt thereof, to a site in a patient suffering from a disease, wherein said site is in need of treatment with the NSAID, comprising topically administering an amount of the NSAID effective for treating the site, and an amount of hyaluronic acid or a pharmaceutically acceptable salt thereof in excess of 200 mg, wherein the hyaluronic acid or pharmaceutically acceptable salt thereof has a molecular weight less than 750,000 daltons but greater than 150,000 daltons.

2. A method of decreasing side effects which would be expected to arise from administration of a non-steroidal anti-inflammatory drug (NSAID) to a patient suffering from a disease and in need of said administration, wherein said side effects are selected from the group consisting of gastrointestinal distress, neurological abnormalities, and depression, comprising topically administering to the patient an amount of the NSAID effective for treating the disease, and an amount of hyaluronic acid or a pharmaceutically acceptable salt thereof in excess of 200 mg, wherein the hyaluronic acid or pharmaceutically acceptable salt thereof has a molecular weight less than 750,000 daltons but greater than 150,000 daltons.

3. A method of treating anorectal disease comprising topically administering to anorectal tissue in need of such treatment a composition comprising a therapeutically effective amount of a drug useful for treating anorectal disease, and an amount of hyaluronic acid or a pharmaceutically acceptable salt thereof, wherein the hyaluronic acid or pharmaceutically acceptable salt thereof constitutes 2% by weight of the composition, and has a molecular weight less than 750,000 daltons but greater than 150,000 daltons.

4. The method of claim 3 wherein the drug useful for treating anorectal disease is an anti-inflammatory drug.

5. The method of claim 4 wherein the anti-inflammatory drug is a non-steroidal anti-inflammatory drug (NSAID).

6. The method of claim 3 wherein the anorectal disease is selected from the group consisting of a tumor and chronic infection.

* * * * *